United States Patent
Randell et al.

(10) Patent No.: US 11,179,056 B2
(45) Date of Patent: Nov. 23, 2021

(54) SYSTEMS AND METHODS FOR SURGICAL GUIDE FOR REAL-TIME MRI SURGERY

(71) Applicant: Wisconsin Alumni Research Foundation, Madison, WI (US)

(72) Inventors: Caitlin R. Randell, Madison, WI (US); Zachary L. Hite, Madison, WI (US); Molly E. De Mars, Madison, WI (US); Bailey J. Ramesh, Madison, WI (US); Mark S. Nyaeme, Elburn, IL (US); Haley A. Yagodinski, Madison, WI (US); Terrence Oakes, Middleton, WI (US); Azam Ahmed, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 608 days.

(21) Appl. No.: 16/100,605

(22) Filed: Aug. 10, 2018

(65) Prior Publication Data

US 2020/0046249 A1 Feb. 13, 2020

(51) Int. Cl.
*A61B 5/055* (2006.01)
*A61B 34/20* (2016.01)
(Continued)

(52) U.S. Cl.
CPC .............. *A61B 5/055* (2013.01); *A61B 34/20* (2016.02); *A61B 90/11* (2016.02); *A61B 90/37* (2016.02);
(Continued)

(58) Field of Classification Search
CPC ........ A61B 17/3403; A61B 2017/3403; A61B 2017/3405; A61B 2017/3407;
(Continued)

(56) References Cited

U.S. PATENT DOCUMENTS 5,957,935 A * 9/1999 Brown ................ A61N 5/1007
606/130
8,747,418 B2 6/2014 Qureshi
(Continued)

OTHER PUBLICATIONS

Carpentier, A. et al., "Laser thermal therapy: Real-time MRI-guided and computer controlled procedures for metastatic brain tumors," Lasers Surg. Med., vol. 43, No. 10, pp. 943-950, Nov. 2011.
(Continued)

*Primary Examiner* — Martin T Ton
(74) *Attorney, Agent, or Firm* — Quarles & Brady LLP

(57) ABSTRACT

A system and method are provided for a guide system for guiding an interventional medical instrument toward a region of interest (ROI) along a predetermined trajectory path. The guide system comprises a base, an adjustment ring, and a plurality of guide blocks. The adjustment ring is configured to be selectively fixed in one of a plurality of rotational orientations with respect to the base. The plurality of guide blocks are each configured to be selectively fixed in one of a plurality of rotational orientations with respect to the adjustment ring and each include a guide hole. Each of the plurality of guide blocks include at least one of differing angles of trajectory or differing locations of the guide hole from others of the plurality of guide blocks to provide a selectable, predetermined location of the guide hole and angle of trajectory.

26 Claims, 19 Drawing Sheets

(51) Int. Cl.
*A61B 90/00* (2016.01)
*A61B 90/11* (2016.01)
*A61B 5/00* (2006.01)
*A61B 34/00* (2016.01)
*A61B 17/34* (2006.01)

(52) U.S. Cl.
CPC .............. *A61B 90/39* (2016.02); *A61B 5/004* (2013.01); *A61B 34/25* (2016.02); *A61B 2017/3407* (2013.01); *A61B 2034/2074* (2016.02); *A61B 2090/374* (2016.02)

(58) Field of Classification Search
CPC .... A61B 2017/3409; A61B 2017/3411; A61B 2017/3413; A61B 90/10; A61B 90/11; A61B 90/14; A61B 2090/103; A61F 2/2875; A61N 1/0539
See application file for complete search history.

(56) References Cited

U.S. PATENT DOCUMENTS

| | | | |
|---|---|---|---|
| 9,222,996 B2 | 12/2015 | Fujimoto | |
| 9,289,270 B2 | 3/2016 | Gielen | |
| 2006/0270902 A1* | 11/2006 | Igarashi | A61B 1/00147 600/114 |
| 2013/0066410 A1* | 3/2013 | Funderburk | A61F 2/2875 607/116 |
| 2014/0024927 A1 | 1/2014 | Piferi | |
| 2015/0366548 A1* | 12/2015 | Lauchner | A61B 17/0218 600/206 |
| 2016/0367331 A1 | 12/2016 | Nelson | |
| 2017/0007349 A1* | 1/2017 | Solar | A61B 17/00234 |
| 2020/0078130 A1* | 3/2020 | Jakab | A61B 90/11 |

OTHER PUBLICATIONS

Chodos A., "MRI Uses Fundamental Physics for Clinical Diagnosis," American Physical Society. [Online].Jul. 2006. Available: https://www.aps.org/publications/apsnews/200607/history.cfm.

De Salles, A.A et al., "Functional Neurosurgery in the MRI Environment," Min. Inv. Neurosurg. vol. 47, No. 9, pp. 284-289, 2004.

Grindle, C. R., et al. "Preoperative magnetic resonance imaging protocol for endoscopic cranial base image-guided surgery." American journal of otolaryngology 32.6 (2011): 451-454.

Jenkins, K., "Real-time, MRI-guided, Minimally Invasive Neurosurgery," Congress of Neurological Surgeons, Jan. 8, 2015. [Online]. Available: https://www.cns.org/publications/congress-quarterly/congress-quarterly-winter-2015/trends-real-time-mri-guided-minimally.

Kumar R., et al. , "Safety of Orthopedic Implants in Magnetic Resonance Imaging: An Experimental Verification," Wiley InterScience vol. 24. No. 9, pp. 1799-1802, Mar. 2006.

Larson, B.T. et al., "Design of an MRI-Compatible Robotic Stereotactic Device for Minimally Invasive Interventions in the Breast," J. Biomech. Eng. vol. 126, No. 4, pp. 458-465, Sep. 2004.

Medtronic.com (2013). Cranial Solutions [Online]. Available FTP: http://www.medtronic.com/content/dam/medtronic-com-m/mdt/neuro/documents/biopsy-sales-sheet.pdf.

Mriinterventions.com. (2017). ClearPoint System Overview [Online], Available FTP: http://www.mriinterventions.com/clearpoint/clearpoint-overview.

Thervoyant.com. (2017). About [Online], Available FTP: http://www.thervoyant.com/about.

\* cited by examiner

SYSTEMS AND METHODS FOR SURGICAL GUIDE FOR REAL-TIME MRI SURGERY

STATEMENT REGARDING FEDERALLY SPONSORED RESEARCH

N/A

BACKGROUND

The present disclosure relates to systems and methods for image-guided interventional procedures, such as those guided by magnetic resonance imaging ("MRI"). More particularly, the present disclosure relates to systems and methods for setting a trajectory path of an interventional medical instrument during an image-guided, interventional procedure.

Minimally invasive surgery has opened new treatment opportunities for surgeries targeting brain tumors, aneurysms, strokes, and epilepsy and other ailments or traumas. Although minimally invasive surgery is extremely beneficial, the technology used for image-guided surgery, is lacking in efficiency and reproducibility. Furthermore, many systems for facilitating image-guided surgical procedures are highly complex and complicated to utilize or control.

Thus, there is a continuing need for systems and methods for performing image-guided surgical procedures that improves upon the traditional systems and methods currently employed.

SUMMARY

The present disclosure overcomes the aforementioned drawbacks by providing systems and methods for minimally- or low-invasive, surgical guides designed to facilitate image-guided procedures with reduced complexity and improved replication. In particular, the present disclosure provides systems and methods that utilize a guide having an incremental adjustment arrangement of rotational elements, which allows for a multitude of varying but fixed number of trajectory paths for an interventional medical instrument that can be set quickly while maintaining accuracy and facilitating image guidance.

In accordance with one aspect of the disclosure, a guide system is provided for guiding an interventional medical instrument toward a region of interest (ROI) along a predetermined trajectory path. The guide system comprises a base, an adjustment ring, and a plurality of guide blocks. The base is configured to be attached to a subject proximate to the ROI. The adjustment ring is configured to be selectively fixed in one of a plurality of incremental rotational orientations with respect to the base. The plurality of guide blocks are each configured to be selectively fixed in one of a plurality of rotational orientations with respect to the adjustment ring and each include a central axis and a guide hole configured to guide the interventional medical instrument along an angle of trajectory with respect to the central axis of the corresponding guide block. Each of the plurality of guide blocks includes at least one of differing angles of trajectory or differing locations of the guide hole from others of the plurality of guide blocks to provide a selectable, predetermined location of the guide hole and angle of trajectory when a given guide block of the plurality of guide blocks is received in the base.

In accordance with another aspect of the disclosure, a guide system is provided for guiding an elongated medical instrument toward a region of interest along a predetermined trajectory path. The guide system comprises a base, an adjustment ring, a plurality of ring adjustment features, a plurality of guide blocks, and a plurality of block adjustment features. The base is configured to be attached to a subject to receive the elongated medical instrument during an interventional medical procedure. The adjustment ring engages the base. The plurality of ring adjustment controls are configured to selectively fix the adjustment ring in a desired rotational orientation with respect to the base. The plurality of guide blocks each include a central axis and a guide hole configured to guide the interventional medical instrument along an angle of trajectory with respect to the central axis of the corresponding guide block and into the subject to perform the interventional medical procedure. The guide holes of the plurality of guide blocks provide at least one of a different angle of trajectory or a different location within a given guide block. The plurality of block adjustment controls are configured to selectively fix the given guide block in a desired rotational orientation with respect to the adjustment ring to present at least one of a unique angle of trajectory or location of the guide hole through which to receive the elongated medical instrument during the interventional medical procedure.

In accordance with yet another aspect of the disclosure, a method is provided for guiding an elongated medical instrument toward a region of interest in a subject using a guide system and a magnetic resonance imaging (MRI) system. The guide system includes a base, an adjustment ring, and a plurality of guide blocks. Each of the guide blocks includes a central axis and a guide hole configured to guide the elongated medical instrument along an angle of trajectory with respect to the central axis of the corresponding guide block. The method comprises attaching the guide system to the subject proximate the region of interest. The method further comprises obtaining a first set of MRI images using the MRI system to orient the guide system with respect to the region of interest. The method further comprises determining, based on the first set of MRI images, a trajectory path for the elongated medical instrument. The method further comprises selecting a guide block of the plurality of guide blocks based on the determined trajectory path. The method further comprises setting a rotational orientation of the adjustment ring with respect to the base based on the determined trajectory path. The method further comprises setting a rotational orientation of the selected guide block with respect to the adjustment ring based on the determined trajectory path. The method further comprises guiding the elongated medical instrument through the guide hole of the selected guide block toward the region of interest.

In accordance with yet another aspect of the disclosure, a guide system is provided for guiding an interventional medical instrument toward a region of interest (ROI) along a predetermined trajectory path. The guide system includes a base, an adjustment ring, a plurality of detachable trajectory stems, and a plurality of guide blocks. The base is configured to be attached to a subject proximate to the ROI. The adjustment ring is configured to be selectively fixed in one of a plurality of incremental rotational orientations with respect to the base. The plurality of detachable trajectory stems each have a guide hole. The plurality of guide blocks are each configured to be selectively fixed in one of a plurality of incremental rotational orientations with respect to the adjustment ring and including a central axis and a trajectory stem aperture. The trajectory stem aperture is configured to receive a given detachable trajectory stem of the plurality of detachable trajectory stems and orient the corresponding guide hole of the given detachable trajectory stem along an angle of trajectory with respect to the central axis of the corresponding guide block. Each of the plurality of guide blocks includes at least one of differing angles of trajectory or differing locations of the guide hole from others of the plurality of guide blocks to provide a selectable, predetermined location of the guide hole and angle of trajectory when a given guide block of the plurality of guide blocks is received in the base.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
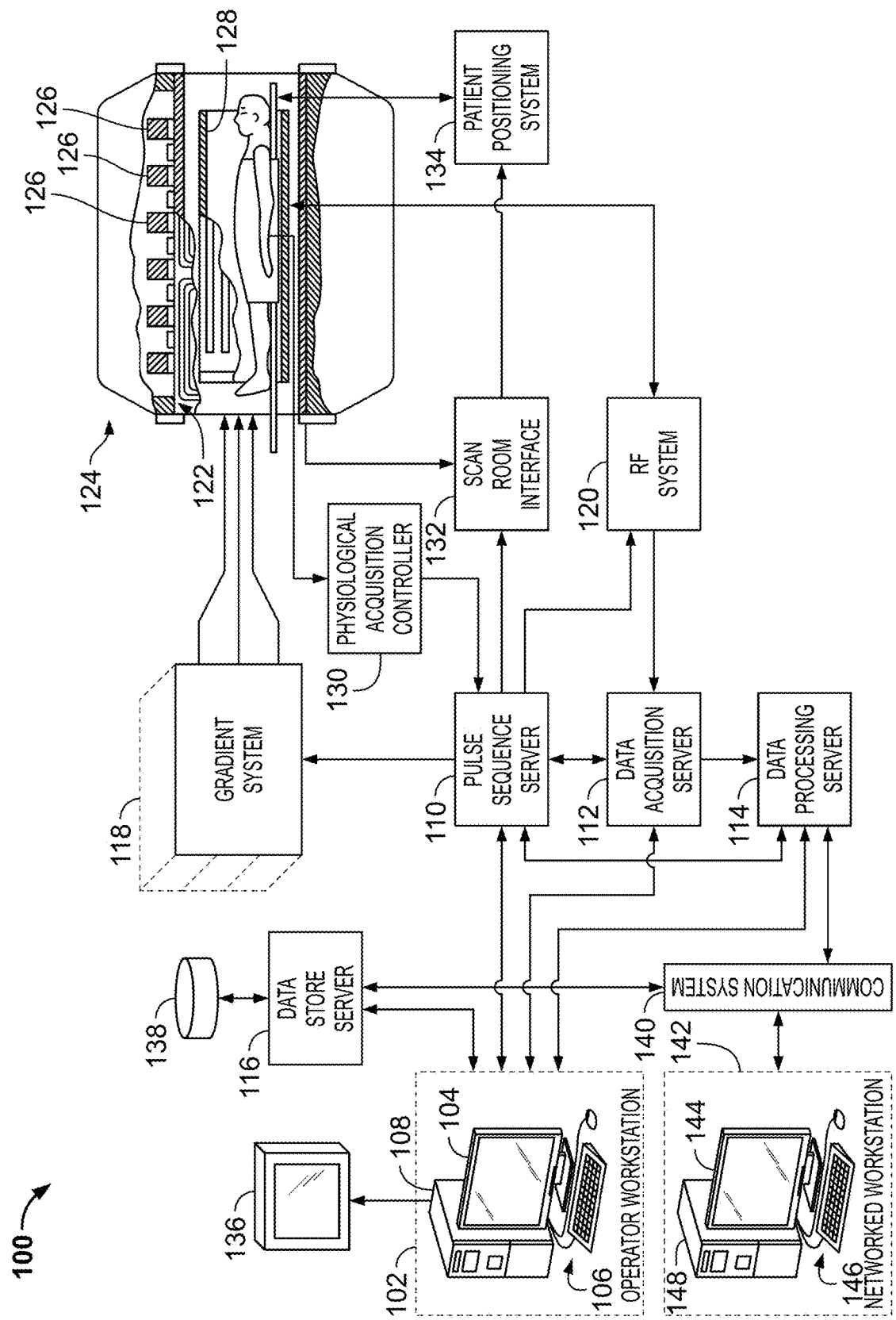
FIG. 1 is a block diagram of an exemplary magnetic resonance imaging ("MRI") system configured in accordance with the present disclosure.

The present disclosure provides various catheter guide systems that may be configured for use with a magnetic resonance imaging ("MRI") system 100, such as is illustrated in FIG. 1.

In the non-limiting example shown in FIG. 1, the MRI system 100 includes an operator workstation 102, which will typically include a display 104, one or more input devices 106 (such as a keyboard and mouse or the like), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers, including a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms to perform the prescribed scan are produced and applied to the gradient system 118, which excites gradient coils in an assembly 122 to produce the magnetic field gradients $G_x$, $G_y$, $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), such as a head coil or any other specific-use coil, in order to perform the prescribed magnetic resonance pulse sequence. Responsive magnetic resonance signals detected by the RF coil 128, or a separate local coil, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. Each RF receiver channel includes an RF preamplifier that amplifies the magnetic resonance signal received by the coil 128 to which it is connected, and a detector that detects and digitizes the/and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2}$$ Eqn. 1;

and the phase of the received magnetic resonance signal may also be determined according to the following relationship:

$$\varphi = \tan^{-1}\left(\frac{Q}{I}\right).$$ Eqn. 2

The pulse sequence server 110 also optionally receives subject data from a physiological acquisition controller 130. By way of example, the physiological acquisition controller 130 may receive signals from a number of different sensors connected to the subject, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the subject and the magnet system. It is also through the scan room interface circuit 132 that a subject positioning system 134 receives commands to move the subject to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during pre-scans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction techniques, such as iterative or back-projection reconstruction techniques; applying filters to raw k-space data or to reconstructed images; generating functional magnetic resonance images; calculating motion or flow images; and so on.

Images reconstructed by the data processing server 114 are conveyed back to the operator workstation 102. Images may be output to operator display 104 or a display 136 that is located near the magnet assembly 124 for use by attending clinician. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse or the like), and a processor 148. The networked workstation 142 may be located within the same facility as the operator workstation 102, or in a different facility, such as a different healthcare institution or clinic. The networked workstation 142 may include a mobile device, including phones or tablets.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

The above-described system may be configured or otherwise used to carry out processes in accordance with the present disclosure. In particular, as will be described in further detail, one aspect for using the above-described or similar systems for carrying out processes in accordance with the present disclosure includes scanning a subject to orient a catheter guide system with respect to a region of interest prior to setting an insertion configuration of the catheter guide system for a subsequent scan in accordance with the present disclosure.

Figure 2:
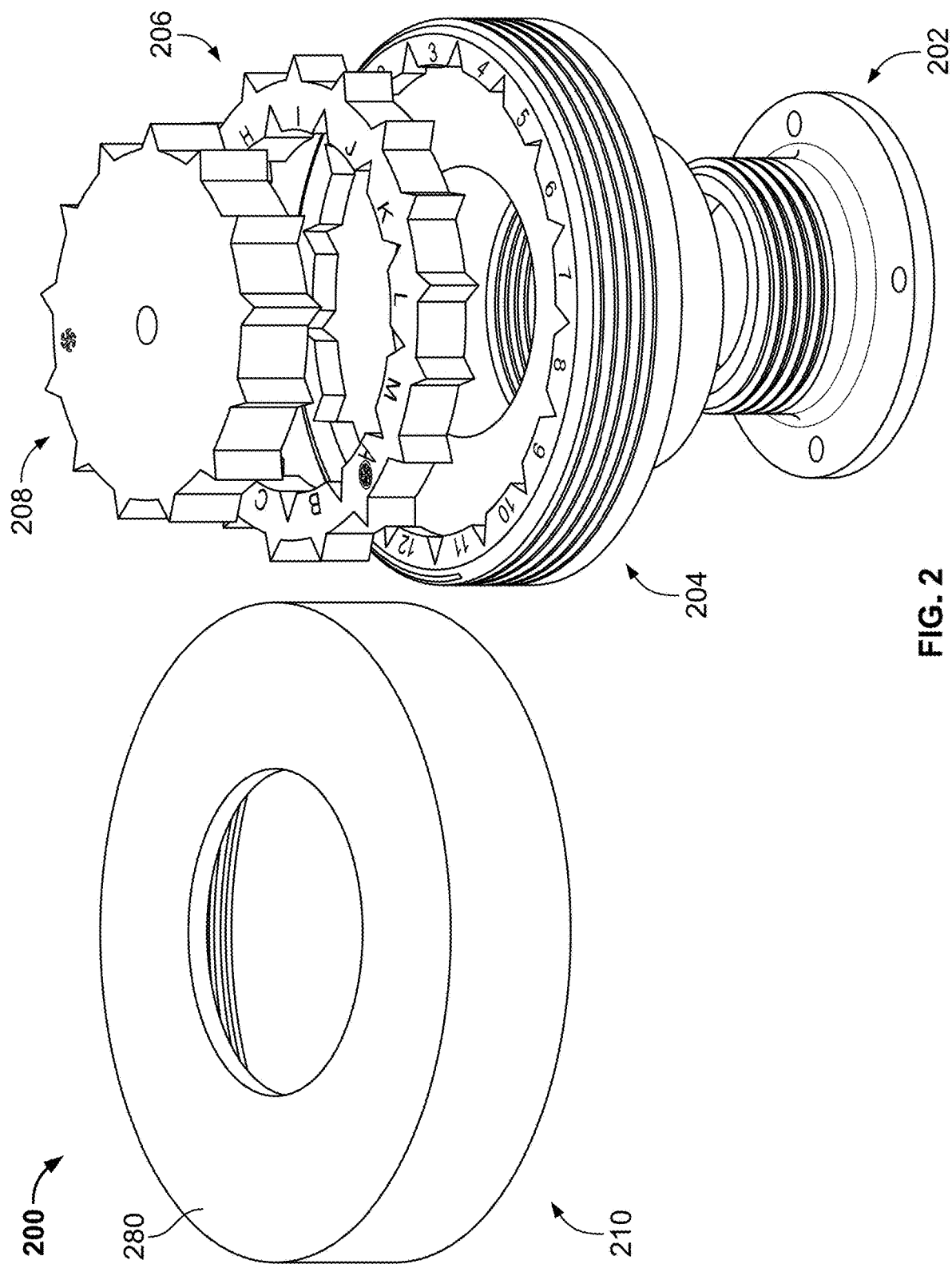
FIG. 2 is an exploded view of a guide system in accordance with the present disclosure.

Referring now to FIG. 2, a guide system 200 in accordance with the present disclosure is illustrated. The guide system 200 may be configured to provide a multitude of potential insertion trajectories for various interventional medical instruments, which may comprise diagnostic, interventional, or therapeutic devices to any desired internal region of a body or other object using the MRI system 100 described above.

In the non-limiting example shown in FIG. 2, the guide system 200 includes a base 202, a ring holder component 204, an adjustment ring 206, a guide block 208, and a cap 210. Each of the components of the guide system 200, including the base 202, the ring holder component 204, the adjustment ring 206, the guide block 208, and the cap 210, may comprise a radiopaque material, such as polycarbonate, PMMA, Teflon, Nylon, Titanium, Tantalum, and Platinum, or any other suitable material, such that the components are compatible with an MRI scan. The guide system 200 may additionally include fiducial markers comprising an MRI-safe and radiopaque material, such as, for example, Vitamin E, Tantalum, or any other suitable MR detectable material. It will be appreciated that these exemplary materials are limited by their MRI scan compatibility. When the guide system 200 is used in procedures which do not include an MRI scan, a wider or modified range of materials are available.

Figure 3:
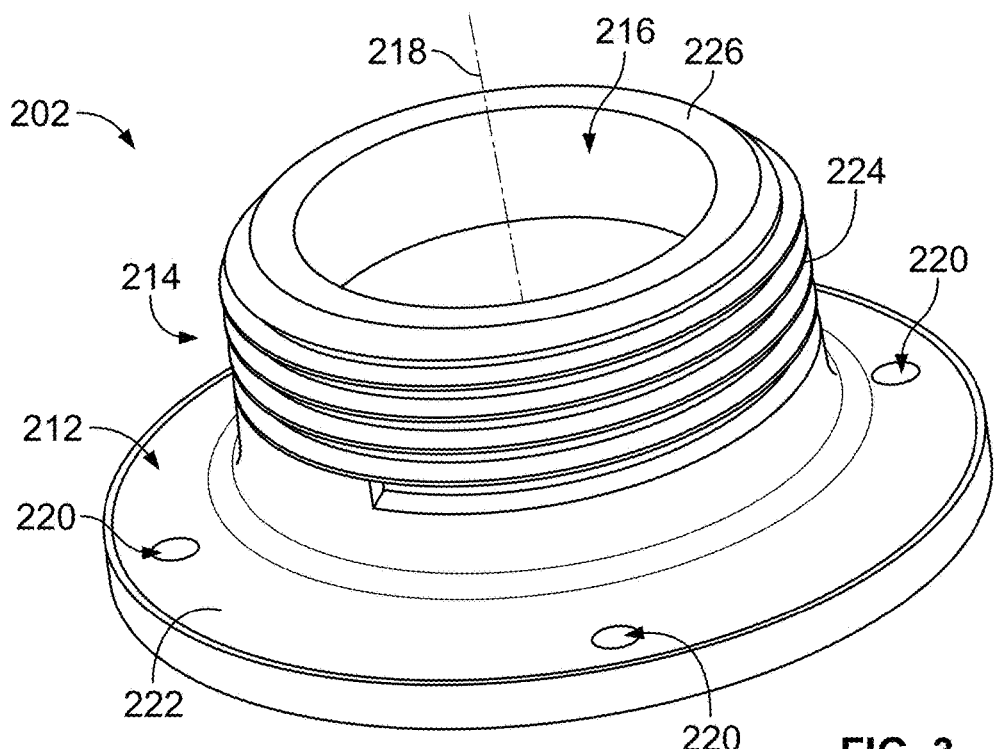
FIG. 3 is a perspective view of a base of the guide system of FIG. 2, in accordance with the present disclosure.

Referring now to FIG. 3, the base 202 includes a base flange 212, a connection portion 214, and a port aperture 216. The base flange 212 defines a generally annular shape, extending radially outward, with respect to a central axis 218 of the base 202, from a lower end 219 of the connection portion 214. The base flange 212 includes a plurality of bone-screw apertures 220 configured to receive a plurality of bone screws 221 (shown in FIG. 8) that may be used to attach the base 202 to the skull or any other anatomical feature of a subject. As illustrated, the bone-screw apertures 220 are evenly-spaced around the circumference of the base flange 212. In some instances, the bone-screw apertures 220 can be unevenly-spaced around the circumference of the base flange 212 as desired for a given operation.

The connection portion 214 defines a generally cylindrical shape, extending upward, along the central axis 218, from an upper surface 222 of the base flange 212. The connection portion 214 includes a radially-outward facing surface 224 that is threaded for coupling the base 202 to the ring holder component 204, as will be described below.

The port aperture 216 extends, along the central axis 218, from an upper surface 226 of the connection portion 214, through the base 202, and through a lower surface 227 (shown in FIG. 8) of the base flange 212. As such, the port aperture 216 forms a cylindrical opening through the entirety of the base 202.

Figure 4:
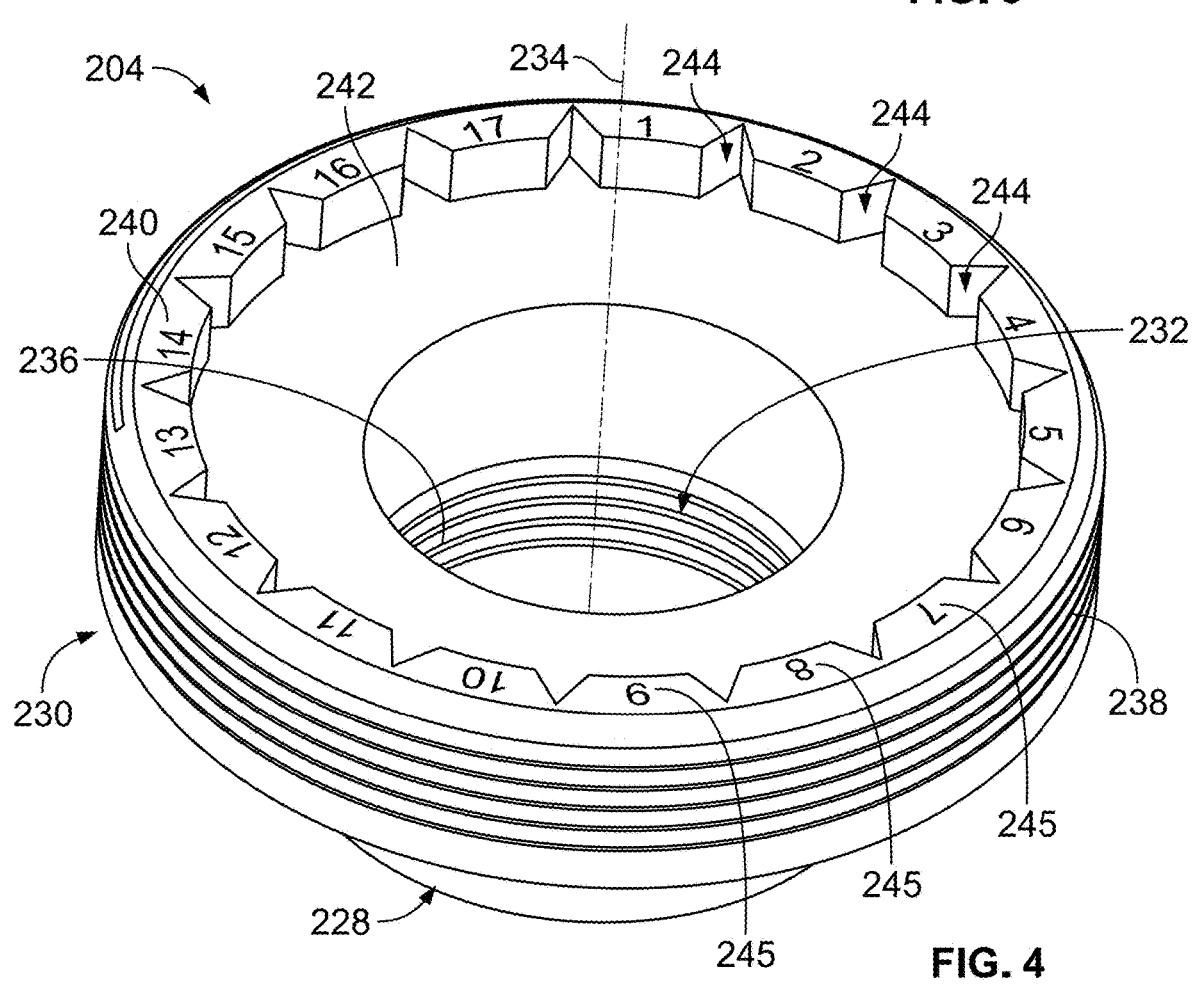
FIG. 4 is a perspective view of a ring holder component of the guide system of FIG. 2, in accordance with the present disclosure.

Referring now to FIG. 4, the ring holder component 204 includes a connection portion 228, a holder portion 230, and a block holder aperture 232. The connection portion 228 defines a generally cylindrical shape, extending downward, along a central axis 234 of the ring holder component 204, from a lower surface 235 (shown in FIG. 8) of the holder portion 230. The connection portion 228 includes a radially inward facing surface 236 that is threaded for coupling the ring holder component 204 to the base 202. This coupling is achieved by threading the connection portion 228 of the ring holder component 204 onto the connection portion 214 of the base 202.

The holder portion 230 defines a generally annular shape, extending radially outward, with respect to the central axis 234, from an upper end of the connection portion 228. The holder portion 230 includes a radially-outward facing surface 238 that is threaded for coupling the ring holder component 204 to the cap 210, as will be described below.

The holder portion 230 further includes an upper surface 240 having an adaptor recess 242. The adaptor recess 242 defines a generally circular shape, with a plurality of locating notches 244 extending radially outward, with respect to the central axis 234, from the circumference of the generally circular shape. As such, the adaptor recess 242 is configured to receive the adjustment ring 206, as will be disclosed below.

In some instances, the upper surface 240 may include indicators 245 between each of the plurality of locating notches 244 to aid in the setting of a desired rotational orientation of the adjustment ring 206 relative to the ring holder component 204, and thereby the base 202, during use, as will be described below. In some non-limiting examples, the indicators 245 may comprise letters, numbers, alphanumeric combinations of characters, symbols, or any other suitable indicator.

The block holder aperture 232 extends, along the central axis 234, from the upper surface 240 of the holder portion 230, through the ring holder component 204, and through a lower surface 246 (shown in FIG. 8) of the connection portion 228. As such, the block holder aperture 232 forms a cylindrical opening through the entirety of the ring holder component 204.

Figure 5:
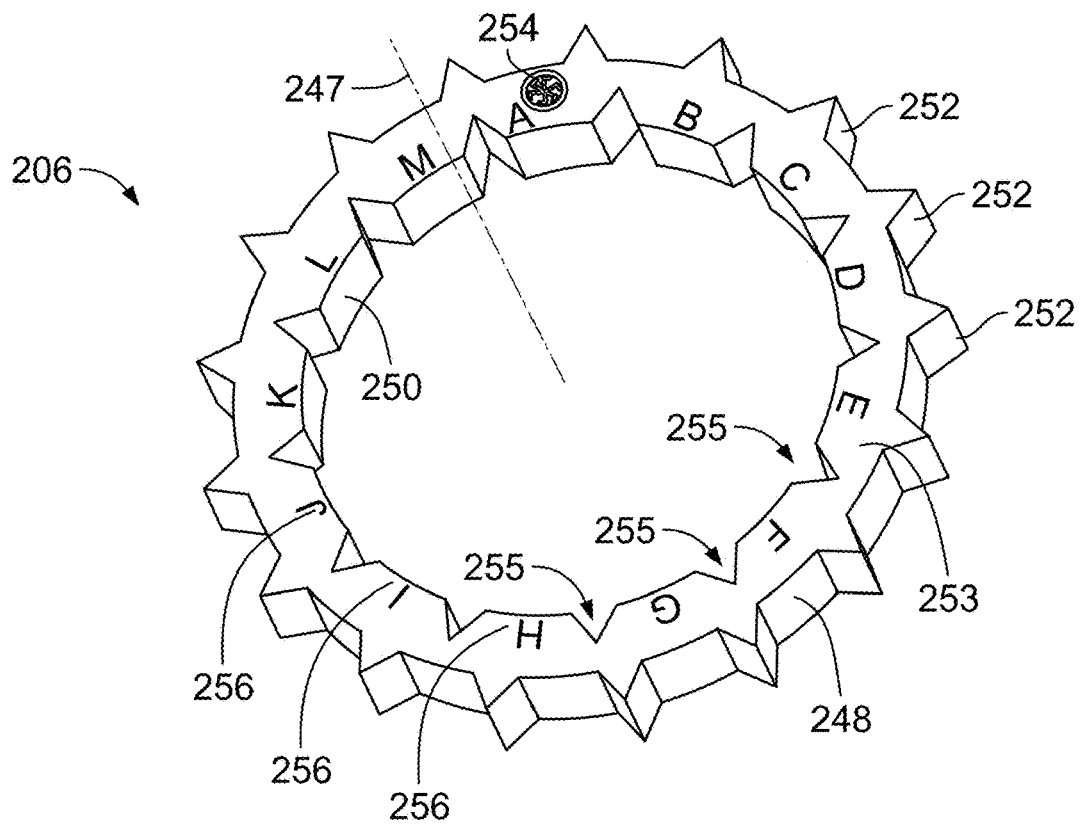
FIG. 5 is a perspective view of an adjustment ring of the guide system of FIG. 2, in accordance with the present disclosure.

Referring now to FIG. 5, the adjustment ring 206 defines a generally annular shape about a central axis 247. The adjustment ring 206 is configured to be received in the adaptor recess 242 of the ring holder component 204. The adjustment ring 206 includes a radially-outward facing surface 248 and a radially-inward facing surface 250.

The radially-outward facing surface 248 includes a plurality of locating protrusions 252. The locating protrusions 252 are configured to engage the plurality of locating notches 244 of the ring holder component 204, thereby providing a plurality of ring adjustment controls configured to selectively fix the adjustment ring 206 with respect to the ring holder component 204 and the base 202. Accordingly, the size, number, and shape of the plurality of locating protrusions 252 of the adjustment ring 206 may correspond to the size, number, and shape of the plurality of locating notches 244 of the ring holder component 204. In some non-limiting examples, it may be beneficial to include a prime number of protrusions 252 and notches 244, such that each protrusion 252 and notch 244 configuration provides a unique orientation of the adjustment ring 206 with respect to the ring holder component 204, as will be described below.

For example, in the illustrated non-limiting example, the plurality of locating protrusions 252 comprises seventeen triangular-shaped protrusions, and the plurality of locating notches 244 correspondingly comprises seventeen triangular-shaped notches. In some non-limiting examples, there can be more or less than seventeen protrusions and/or notches. In some non-limiting examples, the protrusions and/or notches can comprise different shapes, such as, for example, square shapes, rounded shapes, or any other suitable shape.

In some non-limiting examples, an upper surface 253 of the adjustment ring 206 may include an alignment marker 254 configured to be aligned with a predetermined one of the indicators 245 of the ring holder component 204 to orient the adjustment ring 206 with respect to the ring holder component 204, as will be described below. The alignment marker 254 can be an etched mark, a small protrusion, a small recess, or any other suitable marker.

The radially-inward facing surface 250 includes a plurality of locating notches 255. The plurality of locating notches 255 extend outward, with respect to the central axis 247, into the radially-inward facing surface 250. The plurality of locating notches 255 are configured to receive the guide block 208, as will be disclosed below.

In some non-limiting examples, the upper surface 253 of the adjustment ring 206 may further include indicators 256 between each of the plurality of locating notches 255 to aid in the setting of a desired orientation of the guide block 208 relative to the adjustment ring 206 during use, as will be described below. In some non-limiting examples, the indicators 256 may comprise letters, numbers, alphanumeric combinations of characters, symbols, or any other suitable indicator.

Figure 6A:
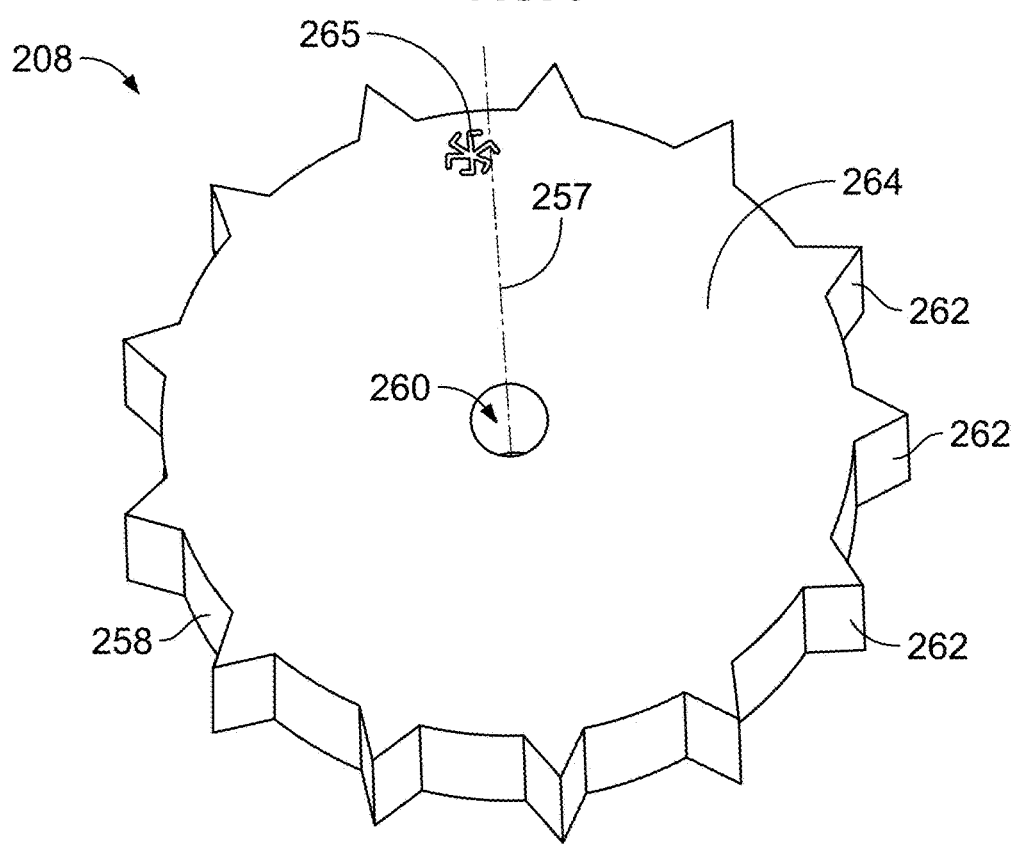
FIG. 6A is a perspective view of a guide block of the guide system of FIG. 2, in accordance with the present disclosure.

Referring now to FIG. 6A, the guide block 208 defines a generally annular shape about a central axis 257 of the guide block 208. The guide block 208 is configured to be received within the adjustment ring 206. The guide block 208 includes a radially-outward facing surface 258 and a guide hole 260.

The radially-outward facing surface 258 includes a plurality of locating protrusions 262. The locating protrusions 262 are configured to engage the plurality of locating notches 255 of the adjustment ring 206, thereby providing a plurality of block adjustment controls configured to selectively fix the guide block 208 with respect to the adjustment ring 206. Accordingly, the size, number and shape of the plurality of locating notches 255 of the adjustment ring 206 may correspond to the size, number, and shape of the plurality of locating protrusions 262 of the guide block 208. In some non-limiting examples, it may again be beneficial to include a prime number of protrusions 262 and notches 255, such that each protrusion 262 and notch 255 configuration provides a unique rotational orientation of the guide block 208 with respect to the adjustment ring 206. It may further be beneficial to include a different prime number of protrusions 262 and notches 255 than the prime number of protrusions 252 and notches 244 between the adjustment ring 206 and the ring holder component 204, such that any protrusion 252 and notch 244 configuration combined with any protrusion 262 and notch 255 configuration provides a unique rotational orientation of the guide block 208 with respect to the ring holder component 204, as will be described below.

For example, in the illustrated non-limiting example, the plurality of locating protrusions 262 comprises thirteen triangular-shaped protrusions, and the plurality of locating notches 255 correspondingly comprises thirteen triangular-shaped notches. In some non-limiting examples, there can be more or less than thirteen protrusions and/or notches. In some non-limiting examples, the protrusions and/or notches can comprise different shapes, such as, for example, square shapes, rounded shapes, or any other suitable shape.

In some non-limiting examples, an upper surface 264 of the guide block 208 may include an alignment marker 265 configured to be aligned with a predetermined one of the indicators 256 of the adjustment ring 206 to orient the guide block 208 with respect to the adjustment ring 206, as will be described below. The alignment marker 265 can be an etched mark, a small protrusion, a small recess, or any other suitable marker.

In the non-limiting example shown in FIG. 6A, the guide hole 260 is disposed centrally on the guide block 208 and extends directly through the guide block 208 from the upper surface 264 of the guide block 208 to a lower surface 266 (shown in FIG. 8) of the guide block 208. That is, the guide hole 260 is concentric and parallel to the central axis 257 of the guide block 208. In some instances, the guide hole 260 can be arranged in other locations on the guide block 208 at angles non-parallel to the central axis 257 of the guide block 208 (e.g., angled guide hole 267 shown in dashed lines on FIG. 8) to achieve differing locations or angles of insertion of a catheter or other elongated object during an operation.

In some instances, the guide system 200 may be provided in a kit including, in addition to the base 202, the ring holder component 204, the adjustment ring 206, and the cap 210, a plurality of guide blocks, each substantially identical to the guide block 208, but having guide holes at differing angles with respect to the central axis of the corresponding guide block. Each guide hole may be disposed at a corresponding location on the guide block, such that, trajectory paths through the guide holes of each of the different guide blocks 208 are configured to pass through a common point proximate the lower surface 227 of the base 202, as will be described below.

Figure 6B:
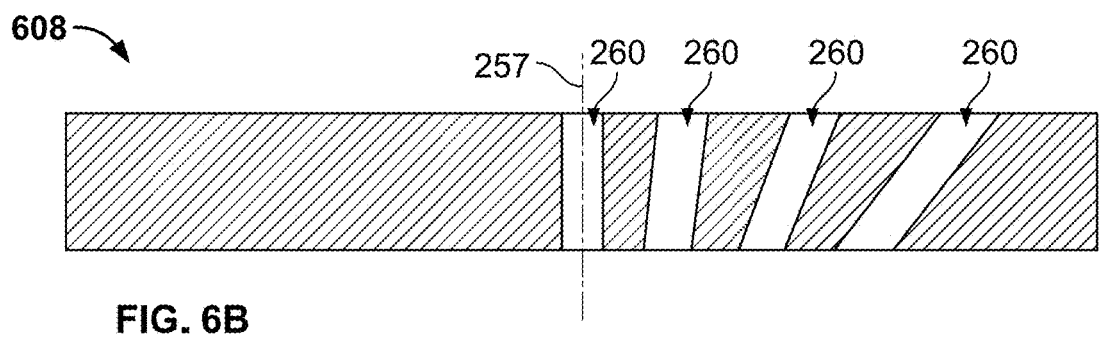
FIG. 6B is a cross-sectional view of another guide block configured for use with the guide system of FIG. 2.

Referring now to FIG. 6B, in some other instances, the guide system 200 may include a guide block 608, substantially similar to the guide block 208, but having a plurality of guide holes 260, each arranged at different angles with respect to the central axis 257.

Figure 7:
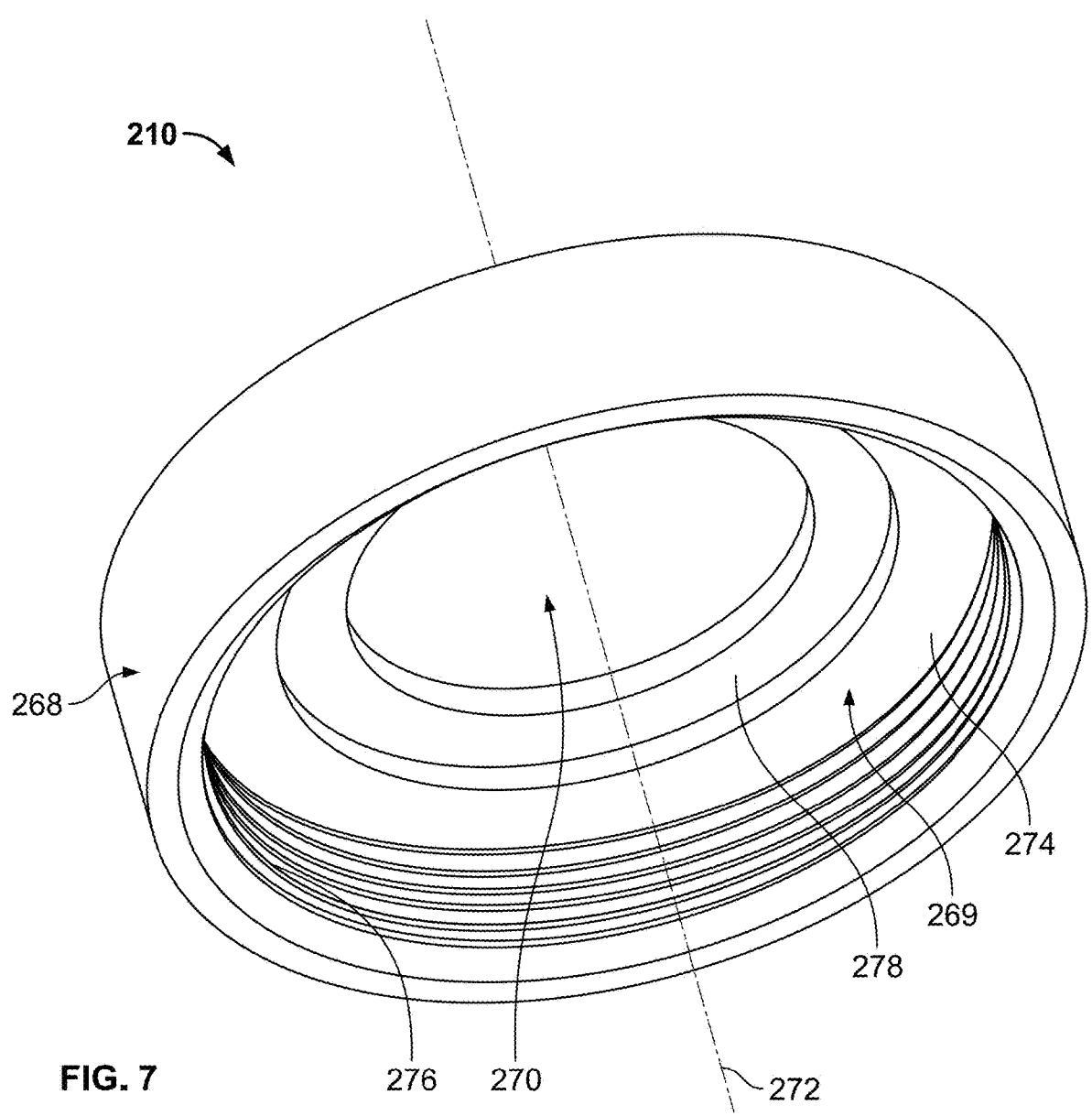
FIG. 7 is a perspective view of a cap of the guide system of FIG. 2, in accordance with the present disclosure.

Referring now to FIG. 7, the cap 210 includes a connection portion 268, an upper portion 269, and a cap aperture 270. The connection portion 268 defines a generally hollow cylindrical shape. The connection portion 268 extends downward, along a central axis 272 of the cap 210, from a lower surface 274 of the upper portion 269. The connection portion 268 includes a radially-inward facing surface 276 that is threaded for coupling the cap 210 to the ring holder component 204. This coupling is achieved by threading the connection portion 268 of the cap 210 onto the holder portion 230 of the ring holder component 204.

The upper portion 269 extends radially inward from an upper end of the connection portion 268, terminating at the cap aperture 270. The upper portion 269 includes a recessed surface 278. The recessed surface 278 is recessed into the lower surface 274 of the upper portion 269 and defines a generally circular shape.

The cap aperture 270 extends, along the central axis 272, from an upper surface 280 (shown in FIG. 2) of the upper portion 269, through the upper portion 269, and through the lower surface 274. As such, the cap aperture 270 extends through the upper portion 269, into the hollow cylindrical shape of the connection portion 268, thereby creating an opening through the entirety of the cap 210.

Now that the general structure of the guide system 200 has been described above, an exemplary method of use is provided below. It should be appreciated that the following method of use is provided as an example, and is in no way meant to be limiting. For example, although the method provided below describes using the guide system 200 to guide a catheter along a predetermined trajectory into a region of interest within the brain of a subject, it will be appreciated by those skilled in the art that the guide system 200 can be used to guide other interventional medical instrument into regions of interest within other areas of the body of a subject.

Figure 8:
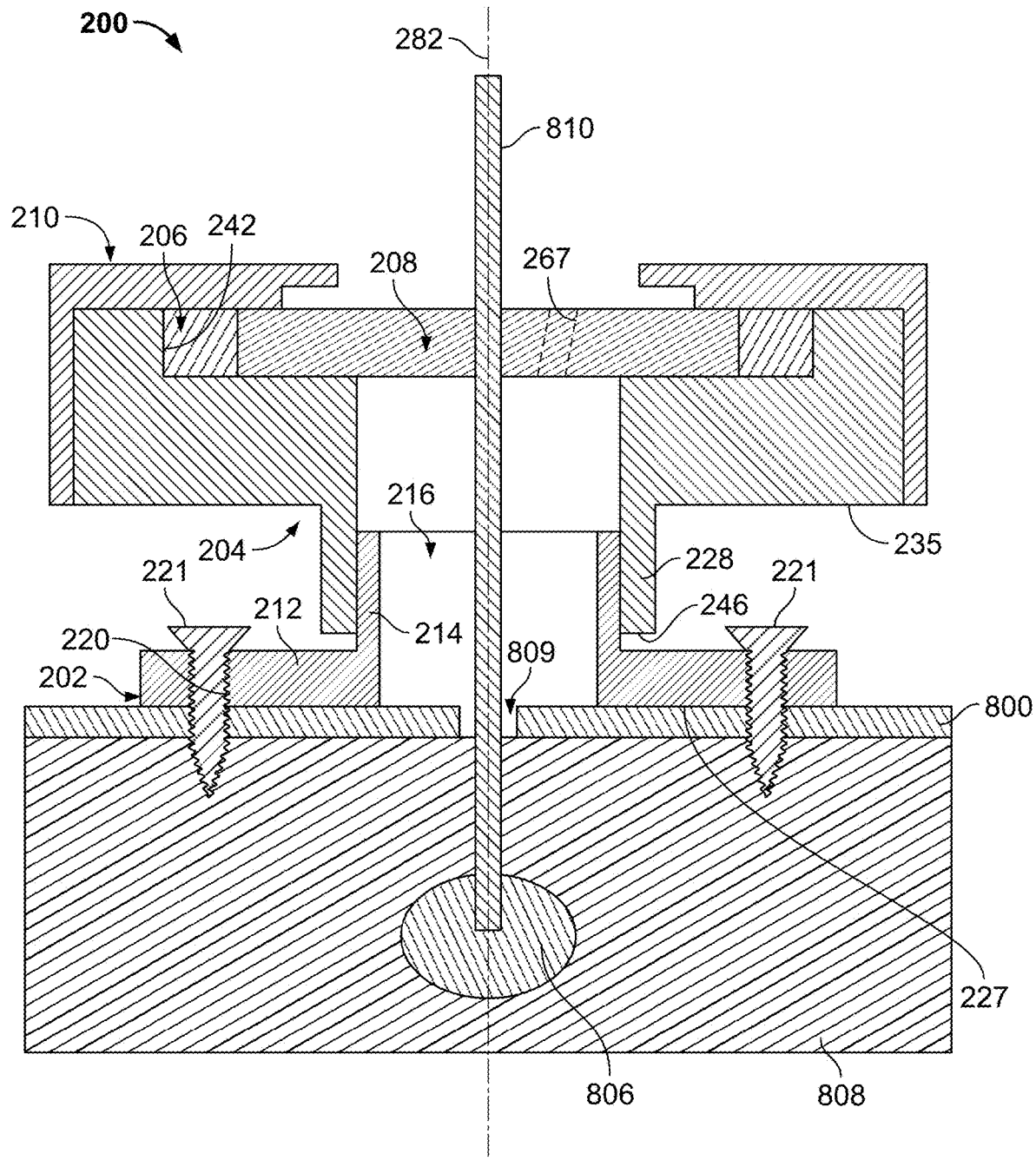
FIG. 8 is a cross-sectional view of the catheter guide system of FIG. 2, shown assembled and attached to a skull of a subject, in accordance with the present disclosure.

Referring now to FIG. 8, during use, a surgeon first arranges the base 202 on the skull 800 in a desired position, based on previously performed scans and surgical planning software. Once the base 202 is arranged on the skull 800, the base 202 can be attached to the skull 800 by screwing bone screws 221 into the skull 800, through the bone-screw apertures 220 in the base flange 212 of the base 202.

With the base 202 attached to the skull 800, the ring holder component 204 can be coupled to the base 202 by threading the connection portion 228 of the ring holder component 204 onto the connection portion 214 of the base 202.

Once the ring holder component 204 is coupled to the base 202, a first MRI scan can be taken using the MRI system 100 described above or any other suitable real-time MRI system. The first MRI scan can be used to orient and locate the guide system 200 in space with respect to a region of interest 806 within a brain 808 of the subject.

Once the guide system 200 has been oriented and located with respect to the region of interest 806, the MRI system 100 may be configured to identify the region of interest 806 within the brain 808 and calculate a list of all trajectories within a desired accuracy that are possible using the guide system 200.

In the non-limiting exemplary guide system 200 provided, the 17 notch/protrusion configurations between the ring holder component 204 and the adjustment ring 206 allow for 17 unique orientations of the adjustment ring 206 relative to the ring holder component 204. Similarly, the 13 notch/protrusion configurations between the adjustment ring 206 and the guide block 208 allow for 13 unique orientations of the guide block 208 relative to the adjustment ring 206. As such, the guide block 208 can be oriented in any of 221 unique rotational orientations with respect to the ring holder component 204. Accordingly, this non-limiting example allows for radial accuracy within approximately 1.6°.

As described above, the guide system 200 may include a plurality of substantially identical guide blocks 208 having guide holes 260 of different trajectory angles. For example, the guide system 200 may include a plurality of guide blocks 208 having guide holes 260 varying in 0.5° increments from 0° to 15° with respect to the central axis 257 of the guide block 208. When assembled, the central axes 218, 234, 247, 257, 272 of the base 202, the ring holder component 204, the adjustment ring 206, the guide block 208, and the cap 210 are coaxially arranged, collectively forming a central axis 282 of the guide system 200. As such, the system 200 may include 31 total guide blocks 208, each having a unique angle of trajectory with respect to the central axis 282 of the guide system 200.

Figure 9:
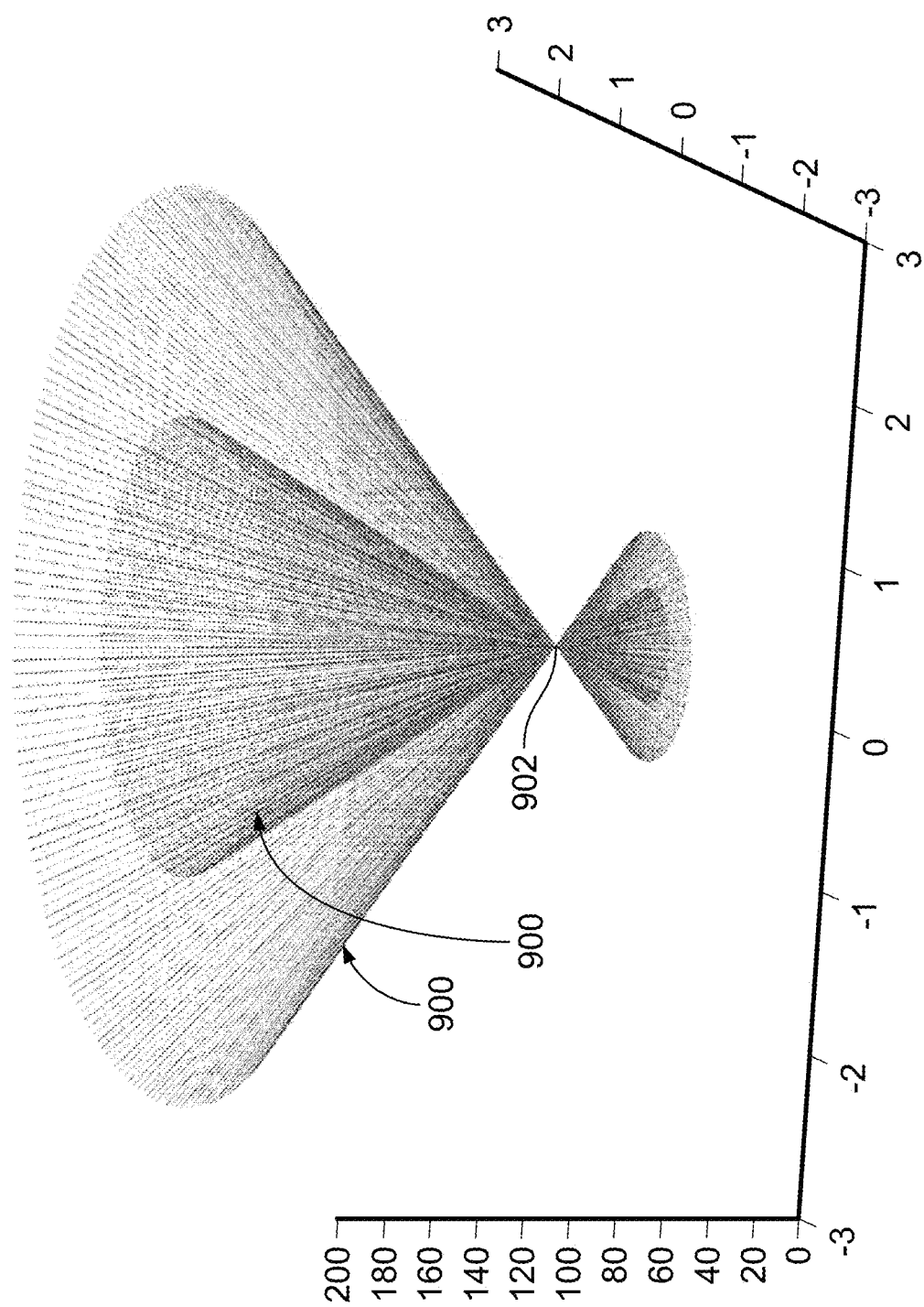
FIG. 9 is a three-dimensional plot showing the potential insertion configurations of two possible insertion angles of a catheter guide system in accordance with the present disclosure.
Figure 10:
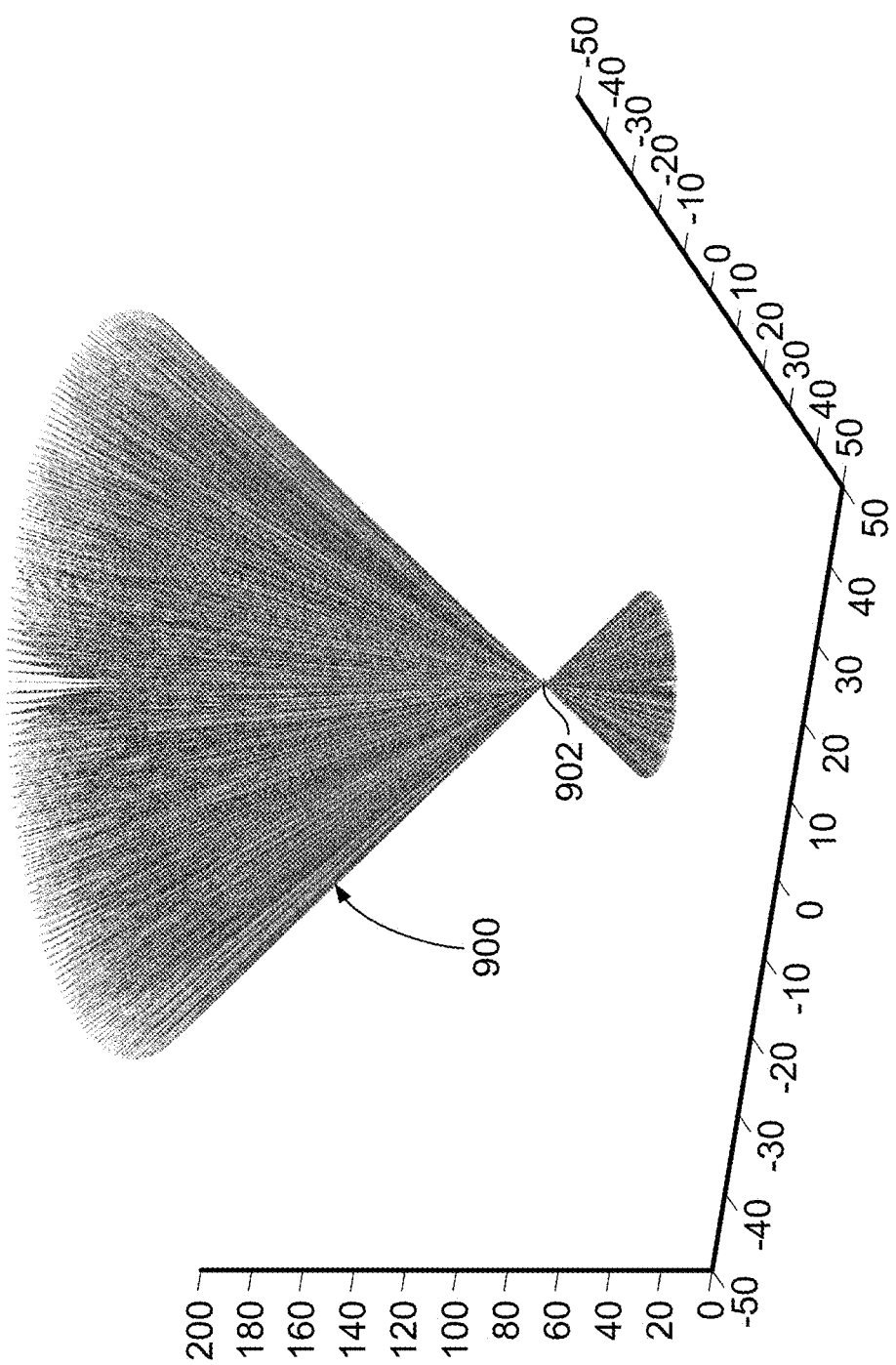
FIG. 10 is a three-dimensional plot showing of the potential insertion configurations of a catheter guide system in accordance with the present disclosure.

Referring to FIGS. 9 and 10, trajectory paths 900 for all 221 unique rotational orientations are shown for 2 potential angles of trajectory (FIG. 9) and 31 potential angles of trajectory (FIG. 10). As can be seen, each of the trajectory paths 900 is oriented to pass through a common point 902. The system 200 may be configured such that this common point 902 coincides with a burr hole 809 to be drilled in the system 200, when the system 200 is attached to the subject, as described below.

The guide system 200 may be configured to provide 6,851 unique trajectory paths (i.e., 221 unique rotational orientations multiplied by the 31 unique angles of trajectory). However, it will be appreciated by those skilled in the art that the number of unique rotational orientations depends on both the number of notches/protrusions between the adjustment holder block 204 and the adjustment ring 206 and the number of notches/protrusions between the adjustment ring 206 and the guide block 208. Similarly, the number of unique trajectory angles may depend on the number of guide blocks 208 provided with the system 200 or, in some instances, the number of guide holes included on a single guide block 208. Accordingly, in some instances, the guide system 200 may be configured to provide more or less than 6,851 unique trajectory paths, which may provide a trajectory accuracy of approximately 0.5 mm at a catheter depth of 120 mm into the subject.

Once the MRI system 100 identifies the region of interest 806 within the brain 808 and calculates a list of all trajectories within the desired accuracy that are possible using the guide system 200, the various trajectories can be graphically represented to the surgeon via the display 136 or any other suitable method, and the surgeon can then choose a desired trajectory path that may avoid major brain structures. In some instances, this decision may be aided by combining the graphically represented trajectories with scans containing protected areas of the brain or other organs.

Once the desired trajectory path is chosen by the surgeon, the surgeon can choose the guide block 208 with the necessary trajectory angle, and can rotationally orient both the adjustment ring 206 and the guide block 208 with respect to the ring holder component 204 to achieve the desired trajectory path. For instance, rotationally orienting the adjustment ring 206 with respect to the ring holder component 204 may comprise aligning the alignment marker 254 of the adjustment ring 206 with a predetermined one of the indicators 245 of the ring holder component 204. Similarly, rotationally orienting the guide block 208 with respect to the adjustment ring 206 may comprise aligning the alignment marker 265 of the guide block 208 with a predetermined one of the indicators 256 of the adjustment ring 206.

With the guide block 208 and the adjustment ring 206 arranged within the adaptor recess 242 of the ring holder component 204, the cap 210 can then be threaded onto the ring holder component 204, thereby locking the guide block 208 and adjustment ring 206 within the adaptor recess 242.

After the surgeon orients the guide system 200 to achieve the desired trajectory path, a second MRI scan can be taken using the MRI system 100 described above or any other suitable real-time MRI system. The second MRI scan can be used to confirm the desired trajectory path in relation to the region of interest 806 within the brain 808.

Once the desired trajectory path is confirmed by the second MRI scan, the surgeon can proceed to drill the burr hole 809 into the skull 800 of the subject, and use the guide system 200 to guide an interventional medical instrument 810 through the guide hole 260 to perform a desired surgery, operation, or treatment. The interventional medical instrument 810 may comprise a catheter or any other diagnostic, interventional, or therapeutic device, as necessary.

Figure 11:
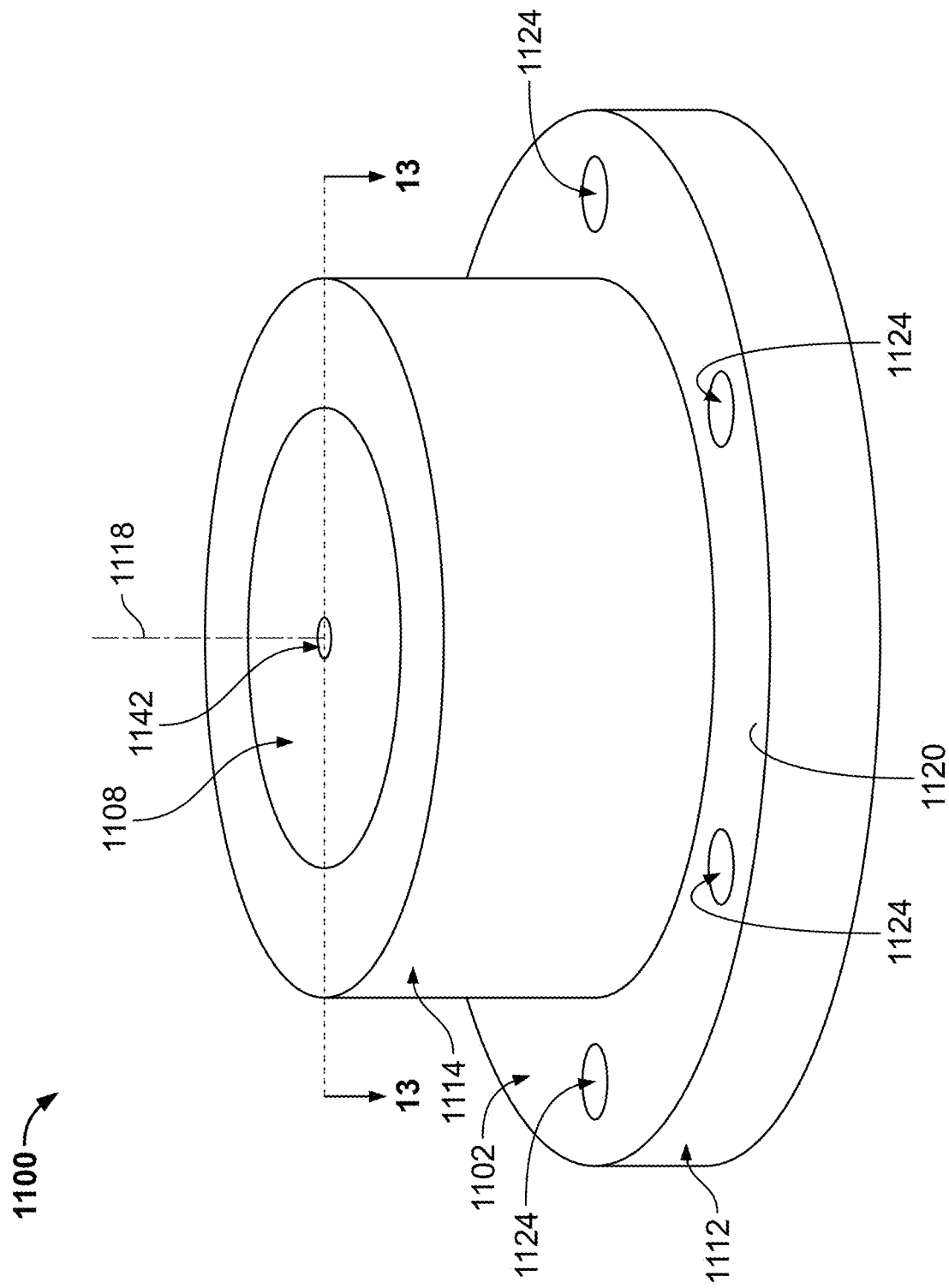
FIG. 11 is a perspective view of another catheter guide system in accordance with the present disclosure.

Referring now to FIG. 11, another guide system 1100 in accordance with the present disclosure is illustrated. The guide system 1100 may similarly be configured to provide a multitude of potential trajectory paths for various diagnostic or interventional devices and/or therapies to any desired internal region of a body or object using the MRI system 100 described above.

Figure 12:
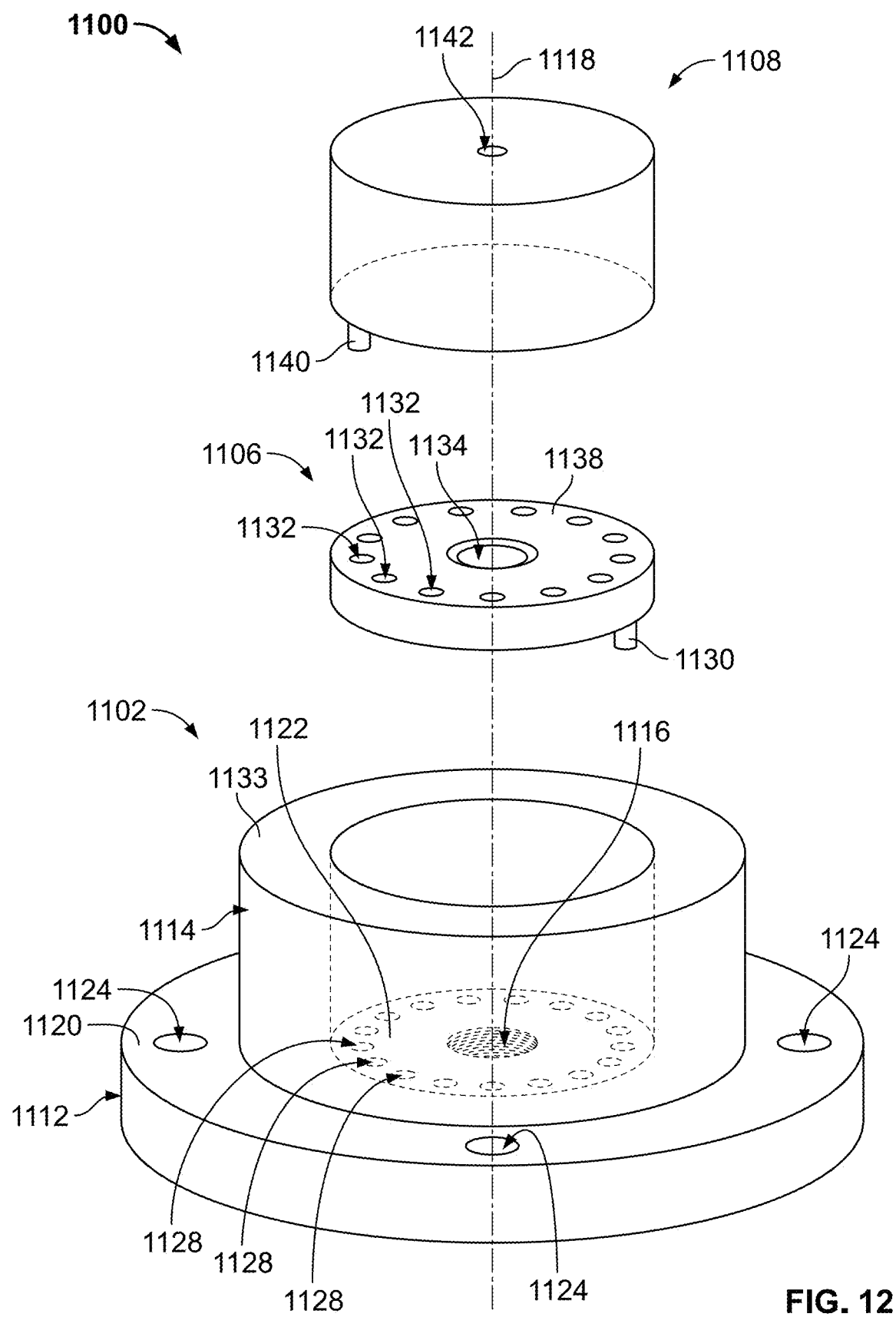
FIG. 12 is an exploded view of the catheter guide system of FIG. 11, in accordance with the present disclosure.

Referring now to FIG. 12, the guide system 1100 includes a base 1102, an adjustment ring 1106, and a guide block 1108. Each of the components of the guide system 1100, including the base 1102, the adjustment ring 1106, and the guide block 1108, may comprise a radiopaque material, such as polycarbonate, PMMA, Teflon, Nylon, Titanium, Tantalum, and Platinum, or any other suitable material, such that the components are compatible with an MRI scan. The system 1100 may be selected to be visible or invisible to MRI. The guide system 1100 may additionally include fiducial markers comprising an MRI-safe and radiopaque material, such as, for example, Vitamin E, Tantalum, or any other suitable MR detectable material. It will be appreciated that these exemplary materials are limited by their MRI scan compatibility. When the guide system 200 is used in procedures which do not include an MRI scan, a wider or modified range of materials are available.

As illustrated, the base 1102 includes a base portion 1112, a hollow cylindrical portion 1114, and a base aperture 1116. The base portion 1112 defines a generally annular shape about a central axis 1118 of the guide system 1100 and includes an outer flange 1120 and an inner flange 1122 (shown in dashed lines). The outer flange 1120 includes a plurality of bone-screw apertures 1124 configured to receive a plurality of bone screws 1126 (shown in FIG. 13) that may be used to attach the base 1102 to the skull or any other anatomical feature of a subject.

The inner flange 1122 includes a plurality of alignment holes 1128 configured to receive an alignment tab 1130 of the adjustment ring 1106, thereby providing a plurality of ring adjustment controls configured to selectively fix the adjustment ring 1106 with respect to the base 1102. The plurality of alignment holes 1128 can be equally-spaced around the periphery of the inner flange 1122. In some instances, there may be a prime number of alignment holes 1128, such that each alignment hole 1128 provides a unique orientation of the adjustment 1106 with respect to the base 1102. For example, in the illustrated non-limiting example, there are seventeen alignment holes 1128. In some other examples, there can be more or less than seventeen alignment holes 1128.

The hollow cylindrical portion 1114 extends upward from the base portion 1112, along the central axis 1118. The hollow cylindrical portion 1114 defines a generally hollow cylindrical shape, configured to receive the adjustment ring 1106 and the guide block 1108 therein.

In some instances, an upper surface 1133 of the hollow cylindrical portion 1114 may include indicators (not shown) aligned with each one of the alignment holes 1128 to aid in the setting of a desired orientation of the adjustment ring 1106 relative to the base 1102 during use, as will be described below. In some non-limiting examples, the indicators may comprise letters, numbers, alphanumeric combinations of characters, symbols, or any other suitable indicator.

The adjustment ring 1106 defines a generally annular shape about the central axis 1118 of the guide system 1100. The adjustment ring 1106 includes the alignment tab 1130, a plurality of alignment holes 1132, and a central aperture 1134. The alignment tab 1130 is configured to engage a predetermined one of the alignment holes 1128 of the base 1102 to set a desired orientation of the adjustment ring 1106 relative to the base 1102.

In some instances, an upper surface 1138 of the adjustment ring 1106 may include an alignment marker (not shown) configured to be aligned with a predetermined one of the indicators of the hollow cylindrical portion 1114 to orient the adjustment ring 1106 with respect to the base 1102, as will be described below. The alignment marker can be an etched mark, a small protrusion, a small recess, or any other suitable marker.

The plurality of alignment holes 1132 are configured to receive an alignment tab 1140 of the guide block 1108, thereby providing a plurality of ring adjustment controls configured to selectively fix the guide block 1108 with respect to the adjustment ring 1106. The plurality of alignment holes 1132 can be equally-spaced around the periphery of the adjustment ring 1106. In some instances, it may again be beneficial to include a prime number of alignment holes 1132, such that each alignment hole 1132 provides a unique orientation of the guide block 1108 with respect to the adjustment ring 1106, as will be described below.

For example, in the illustrated non-limiting example, there are thirteen alignment holes 1132. In some non-limiting examples, there can be more or less than thirteen alignment holes 1132.

In some instances, an upper surface 1138 of the adjustment ring 1106 may include indicators (not shown) at each one of the alignment holes 1132 to aid in the setting of a desired orientation of the guide block 1108 relative to the adjustment ring 1106, as will be described below. In some non-limiting examples, the indicators may comprise letters, numbers, alphanumeric combinations of characters, symbols, or any other suitable indicator.

The guide block 1108 defines a generally annular shape about the central axis 1118 of the guide system 1100. The guide block 1108 includes an alignment tab 1140 and a guide hole 1142. The alignment tab 1140 is configured to engage a predetermined one of the alignment holes 1132 of the adjustment ring 1106 to set a desired orientation of the guide block 1108 relative to the adjustment ring 1106.

In some non-limiting examples, an upper surface 1143 of the guide block 1108 may include an alignment marker (not shown) configured to be aligned with a predetermined one of the indicators of the adjustment ring 1106 or of the upper surface 1133 of the base 1102 to orient the guide block 1108 with respect to the adjustment ring 1106, as will be described below. The alignment marker can be an etched mark, a small protrusion, a small recess, or any other suitable marker.

Figure 13:
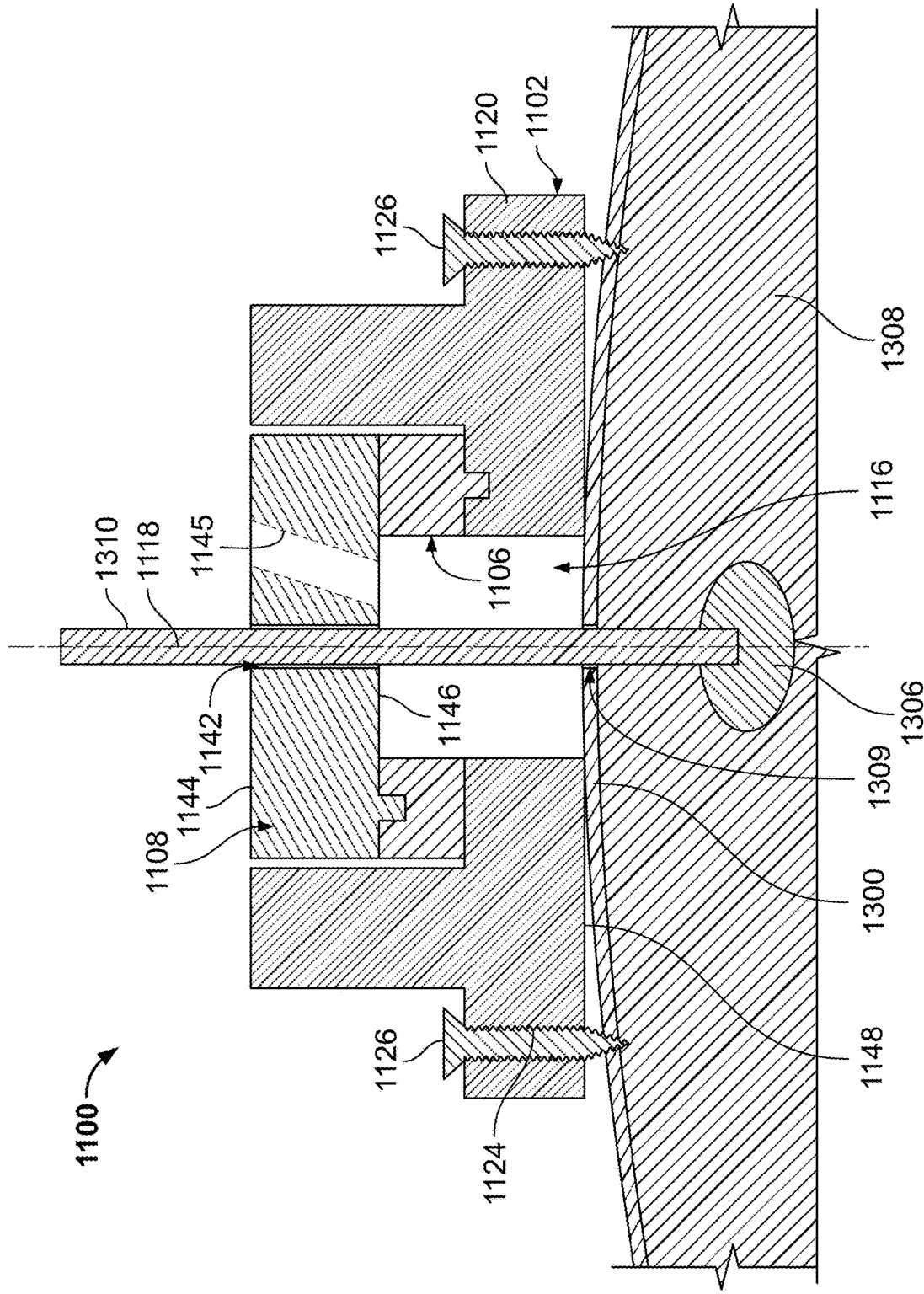
FIG. 13 is a cross-sectional view of the catheter guide system of FIG. 11, taken along line 13-13, shown coupled to a skull of a subject.

Referring now to FIG. 13, the guide hole 1142 is disposed centrally on the guide block 1108 and extends directly through the guide block 1108 from an upper surface 1144 of the guide block 1108 to a lower surface 1146 of the guide block 1108. That is, the guide hole 1142 is concentric and parallel to the central axis 1118 of the guide system 1100. In some instances, the guide hole 1142 can be arranged in other locations on the guide block 1108 at angles non-parallel to the central axis 1118 of the guide system 1100 (e.g., angled guide hole 1145 shown in dashed lines in FIG. 13) to achieve differing angles of insertion of a catheter or other elongated object during an operation.

For example, the guide system 1100, similar to the guide system 200 described above, may be provided in a kit including a plurality of guide blocks, each substantially identical to the guide block 1108, but having guide holes at differing angles with respect to the central axis 1118 of the guide system 1100. Each guide hole may be disposed at a corresponding location on the guide block, such that trajectory paths through the guide holes of every different guide block 1108 are configured to pass through a common point proximate a lower surface 1148 of the base 1102, as will be described below.

Now that the general structure of the guide system 1100 has been described above, an exemplary method of use is provided below. It should again be appreciated that the following method of use is provided as an example, and is in no way meant to be limiting. Further, it should be appreciated that, although the structure of the guide system 1100 varies from that of the guide system 200 described above, the general method of use for the guide system 1100 follows a similar process as that of the guide system 200, and accordingly various components and method steps of the exemplary method described above, with reference to the guide system 200, may also apply to the guide system 1100.

With continued reference to FIG. 13, during use, a surgeon first arranges the base 1102 on the skull 1300 in a desired position, based on previously performed scans and surgical planning software. Once the base 1102 is arranged on the skull 1300, the base 1102 can be attached to the skull 1300 by screwing bone screws 1126 into the skull 1300, through the bone-screw apertures 1124 in the outer flange 1120 of the base 1102.

With the base 1102 attached to the skull 1302, a first MRI scan can be taken using the MRI system 100 described above or any other suitable real-time MRI system. The first MRI scan can be used to orient and locate the guide system 1100 in space with respect to a region of interest 1306 within a brain 1308 of the subject.

Once the guide system 1100 has been oriented and located with respect to the region of interest 1306, the MRI system 100 may be configured to identify the region of interest 1306 within the brain 1308 and calculate a list of all trajectories within a desired accuracy that are possible using the guide system 1100.

In the non-limiting exemplary guide system 1100 provided, the 17 alignment holes 1128 of the inner flange 1122 allow for 17 unique orientations of the adjustment ring 1106 relative to the base 1102. Similarly, the 13 alignment holes 1132 of the adjustment ring 1106 allow for 13 unique orientations of the guide block 1108 relative to the adjustment ring 1106. As such, the guide block 1108 can similarly be oriented in any of 221 unique rotational orientations with respect to the base 1102. Accordingly, this non-limiting example again allows for radial accuracy within approximately 1.6°.

As described above, the guide system 1100 may include a plurality of substantially identical guide blocks 1108 having guide holes 1142 of different trajectory angles. For example, the guide system 1100 may include guide blocks 1108 having guide holes 1142 varying in 0.5° increments from 0° to 15° with respect to the central axis 1118 of the guide system 1100. As such, the system 1100 may include 31 total guide blocks 1108, each having a unique angle of trajectory with respect to the central axis 1118 of the guide system 1100.

Referring again to FIGS. 9 and 10, the guide system 1100 may be configured to provide the same or similar exemplary potential trajectory paths 900 for all 221 unique rotational orientations are shown for 2 potential angles of trajectory (FIG. 9) and 31 potential angles of trajectory (FIG. 10). Similar to the system 200, the system 1100 may be configured such that the common point 902 of all the potential trajectory paths 900 coincides with the burr hole 1309 to be drilled in the system 200, when the system 200 is attached to the subject, as described below.

The guide system 1100 may therefore be configured to provide a similar 6,851 unique trajectory paths (i.e., 221 unique rotational orientations multiplied by the 31 unique angles of trajectory) which may provide a trajectory accuracy of approximately 0.5 mm at a catheter depth of 120 mm into the subject. However, it will be appreciated by those skilled in the art that the number of unique rotational orientations depends on both the number of alignment holes 1128 of the inner flange 1122 of the base 1102 and the number of alignment holes 1132 of the adjustment ring 1106. Similarly, the number of unique trajectory angles may depend on the number of guide blocks 1108 provided with the system or, in some instances, the number of guide holes included on a single guide block 1108. Accordingly, in some instances, the guide system 1100 may be configured to provide more or less than 6,851 unique trajectory paths, which may provide a higher or lower level of trajectory accuracy within the subject, as necessary.

Once the MRI system 100 identifies the region of interest 1306 within the brain 1308 and calculates the list of all trajectories within the desired accuracy that are possible using the guide system 1100, the various trajectories can be graphically represented to the surgeon via the display 136 or any other suitable method, and the surgeon can then choose a desired trajectory path that may avoid major brain structures.

Once the desired trajectory path is chosen by the surgeon, the surgeon can similarly choose the guide block 1108 with the necessary trajectory angle, and can rotationally orient both the adjustment ring 1106 and the guide block 1108 with respect to the base 1102 to achieve the desired trajectory path. For instance, rotationally orienting the adjustment ring 1106 with respect to the base 1102 may comprise aligning the alignment marker of the adjustment ring 1106 with a predetermined one of the indicators of the base 1102. Similarly, rotationally orienting the guide block 1108 with respect to the adjustment 1106 may comprise aligning the alignment marker of the guide block 1108 with a predetermined one of the indicators of the adjustment ring 1106.

After the surgeon orients the guide system 1100 to achieve the desired trajectory path, a second MRI scan can be taken using the MRI system 100 described above or any other suitable real-time MRI system. The second MRI scan can be used to confirm the desired trajectory path in relation to the region of interest 1306 within the brain 1308.

Once the desired trajectory path is confirmed by the second MRI scan is confirmed, the surgeon can proceed to drill the burr hole 1309 into the skull 1300 of the subject, and to use the guide system 1100 to guide an interventional medical instrument 1310 through the guide hole 1142 to perform a desired surgery, operation, or treatment. The interventional medical instrument 1310 may comprise a catheter or any other diagnostic, interventional, or therapeutic device, as necessary.

It should be appreciated that various aspects of the guide systems 200, 1100 disclosed herein may alternatively or additionally include aspects of the other guide system 200, 1100 without departing from the scope of the invention. For example, the guide system 200 includes the base 202, which is threadably attached to the ring holder component 204 receiving the adjustment ring 206 and the guide block 208, while the guide system 1100 includes a base 1102 that directly receives the adjustment ring 1106 and the guide block 1108. In some instances, the guide system 200 may include a base that is configured to directly receive the adjustment ring 206 and the guide block 208. In this instance, the base 202 and the ring holder component 204 may be formed as a single base component.

It should be appreciated that, the guide systems 200, 1100 can include various alternative connection or base portions for connecting the guide systems 200, 1100 to the skull of a subject.

Figure 14A:
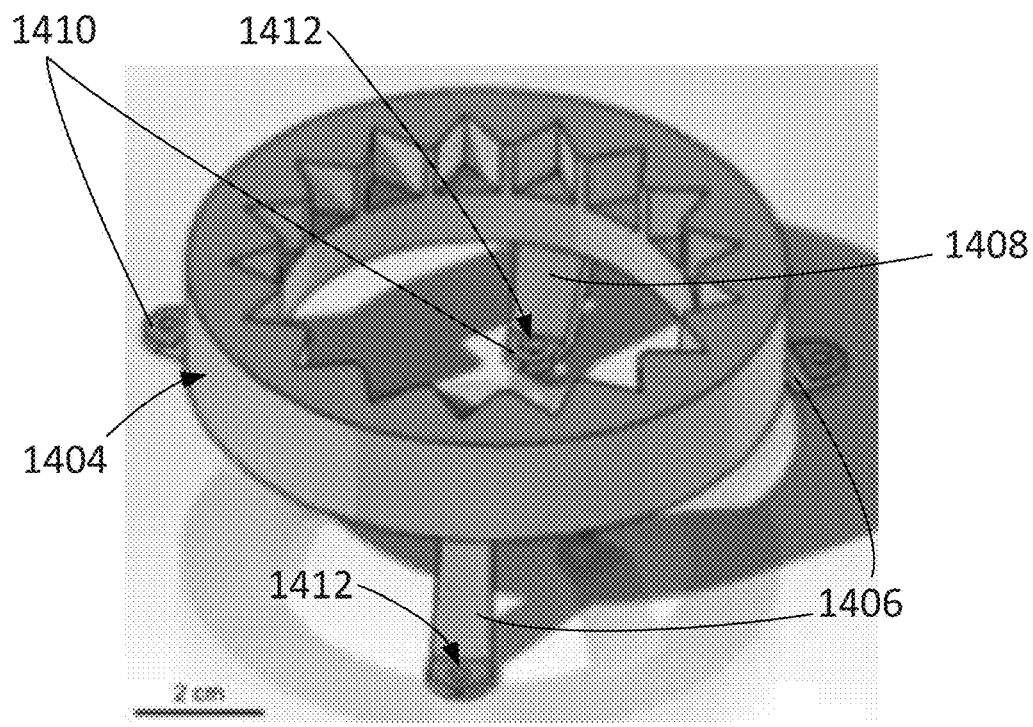
FIG. 14A is a perspective view of a ring holder component of a guide system in accordance with the present disclosure.
Figure 14B:
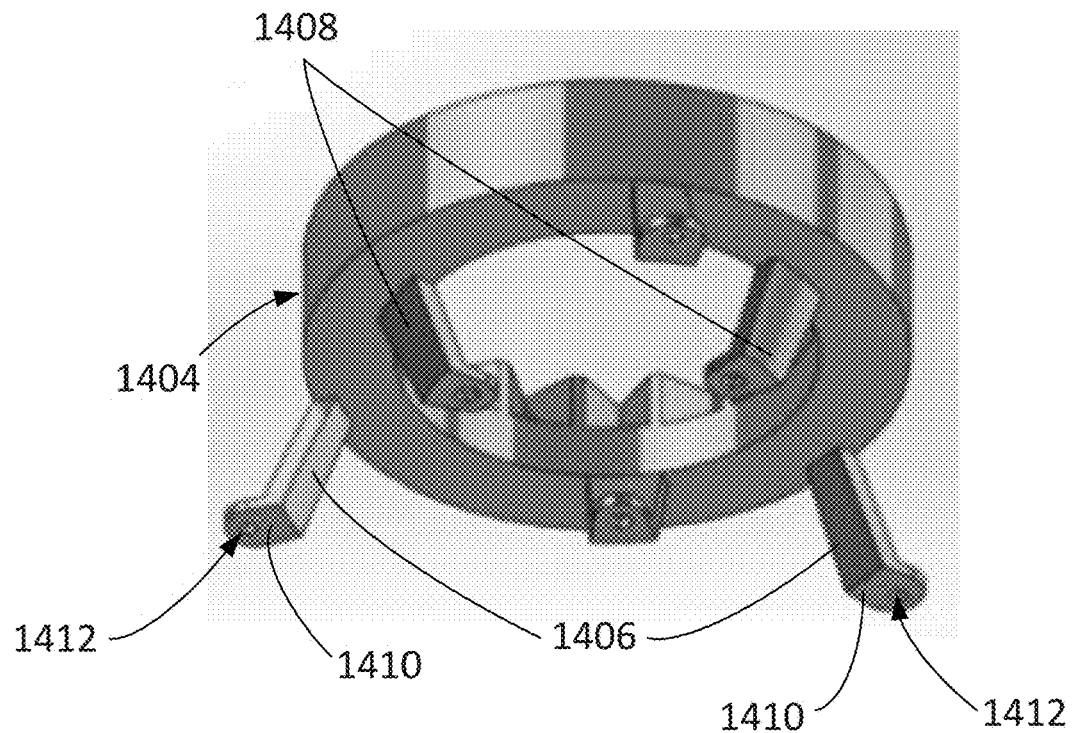
FIG. 14B is a perspective view of the ring holder component of FIG. 14A.

For example, referring now to FIGS. 14A and 14B, a ring holder component 1404 is illustrated, similar to the ring holder component 204, which includes a plurality of outwardly disposed stilts 1406 and a plurality of inwardly disposed stilts 1408. Each of the plurality of outwardly disposed stilts 1406 and each of the plurality of inwardly disposed stilts 1408 include corresponding stilt feet 1410. Each of the stilt feet 1410 include bone screw apertures 1412 configured to receive bone screws to couple the ring holder component 1404 to the skull of a subject.

In some instances, the inwardly disposed stilts 1408 may be of shorter length than the outwardly disposed stilts 1406. In these instances, when the bone screws are screwed into the skull, through the bone screw apertures 1412 of the inwardly disposed stilts 1408, the outwardly disposed stilts 1406 are pulled into contact with the skull by the tightening of the bone screws through the bone screw apertures 1412 of the inwardly disposed stilts 1408. Accordingly, in some instances, the bone screw apertures 1412 on the outwardly disposed stilts 1406 need not be included, allowing for reduced drilling into the skull during surgery. However, in some instances, the bone screw apertures 1412 may be included, and blunt screws may be used to press against the skull to provide additional stability. Further, the addition of the blunt screws used in the outwardly disposed stilts 1406 may allow for the bone screws used in the inwardly disposed stilts 1408 to be only partially screwed into the skull, while maintaining rigidity of the guide system, thereby diminishing potential skull tissue necrosis.

Additionally, because the ring holder component 1404 is raised away from the skull when implanted, skull chips created while drilling may be removed and the entry point or burr hole is more clearly visible.

Figure 15:
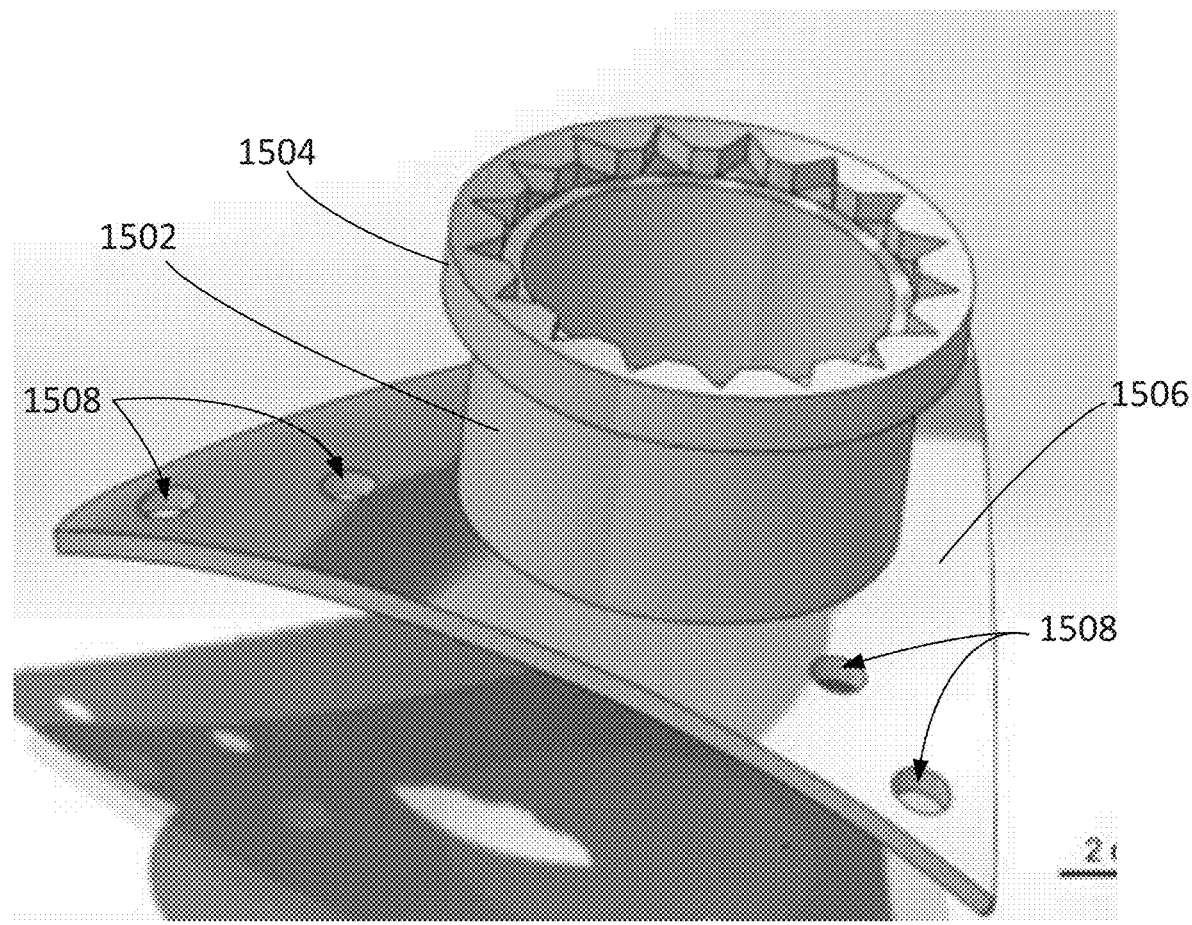
FIG. 15 is a perspective view of a unitarily formed base and ring holder component of a guide system in accordance with the present disclosure.

Referring now to FIG. 15, a base 1502 is illustrated that is unitarily formed with a ring holder component 1504, similar to the ring holder component 204. The base 1502 further includes a flange 1506, which has a curved lower surface configured to conform to the surface of the skull. The flange 1506 has multiple bone screw apertures 1508, configured to receive bone screws to attach the base 1502 to the skull of a subject.

As shown in the non-limiting illustrated example, in some instances, the bone screw apertures 1508 can be arranged in circumferentially-spaced radially-arranged pairs. During implantation, a bone screw may be lightly screwed into the skull within the inner bone screw aperture 1508 of each pair. Then, a blunt screw may be screwed into the corresponding outer bone screw aperture 1508 of each pair to generate tension in the inner bone screws, thereby providing stability to the base 1502. Because the inner bone screws need only be lightly screwed into the skull, this may reduce the likelihood of necrosis.

In some instances, the guide systems 200, 1100 may additionally include a trajectory stem to increase precision and accuracy while either drilling the burr hole in the skull or guiding the interventional medical instrument through the corresponding guide hole. The precision and accuracy may be achieved by elongating the portion of the guide system that guides the drill or instrument, thereby ensuring that the correct trajectory path is maintained.

Figure 16:
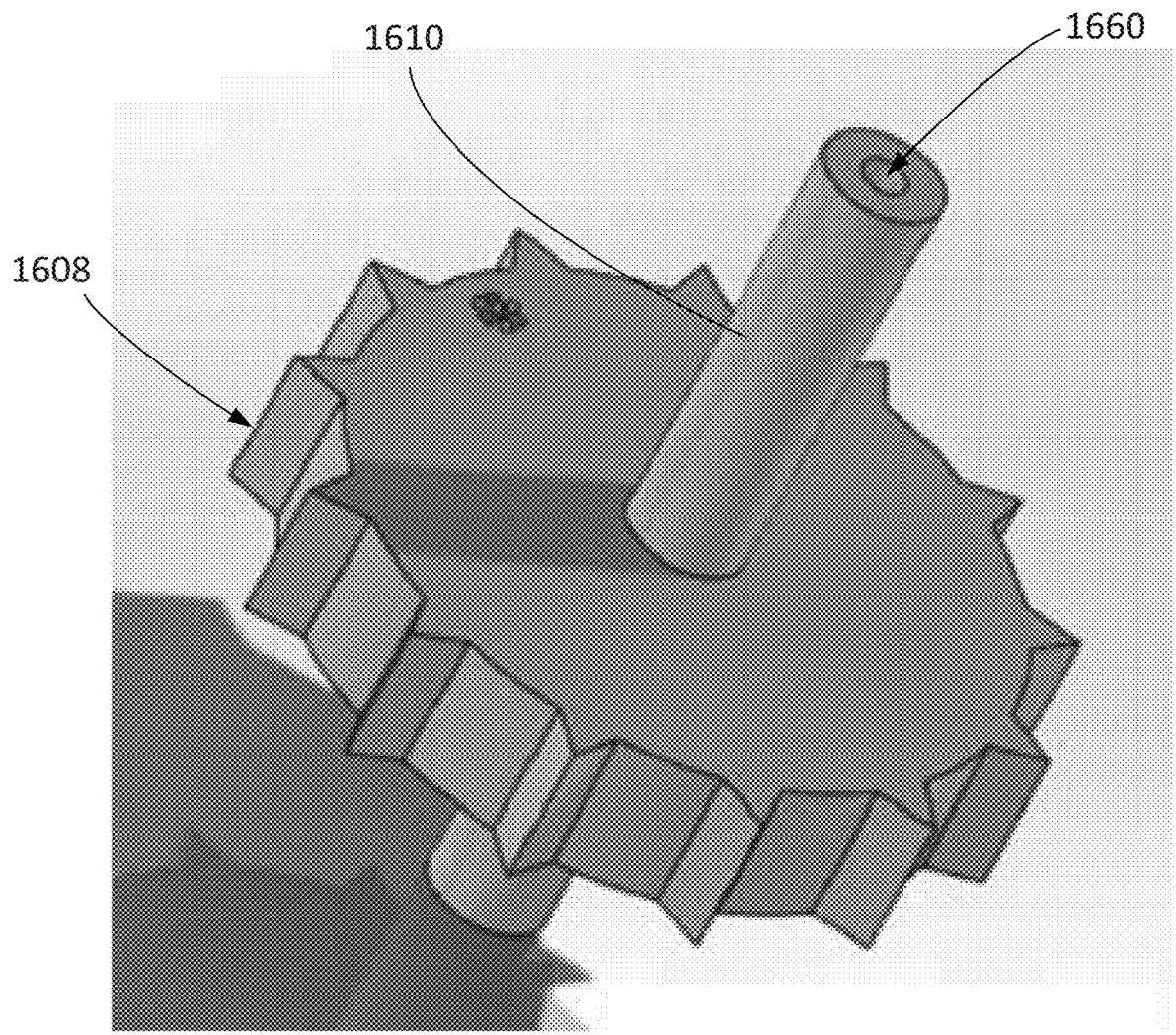
FIG. 16 is a perspective view of a unitarily formed guide block and trajectory stem of a guide system in accordance with the present disclosure.

For example, referring now to FIG. 16, a guide block 1608 is illustrated. The guide block 1608 is similar to the guide block 208, but further includes an integral trajectory stem 1610. The trajectory stem 1610 defines a hollow, cylindrical shape. The guide hole 1660 extends throughout the trajectory stem 1610, and is arranged coaxially within the cylindrical shape of the trajectory stem 1610. Accordingly, the trajectory stem 1610 is configured to effectively elongate the guide hole 1660 of the guide block 1608.

In some instances, it may be desirable to allow for the interchangeability of trajectory stems, to allow for multiple instrument diameters to be guided using a single block.

Figure 17:
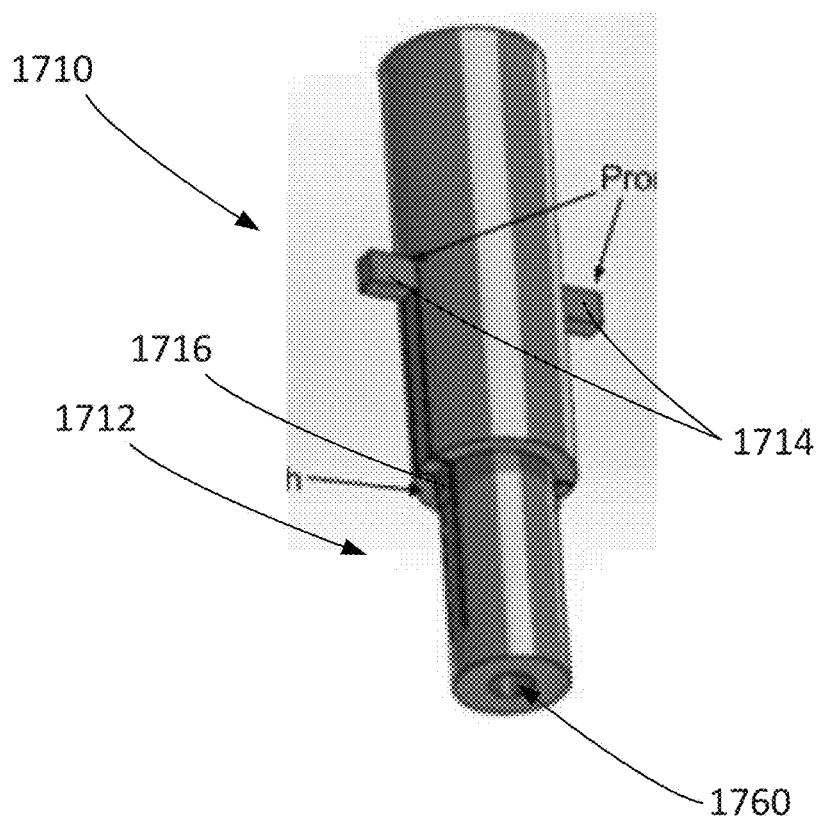
FIG. 17 is a perspective view of a detachable trajectory stem of a guide system in accordance with the present disclosure.
Figure 18:
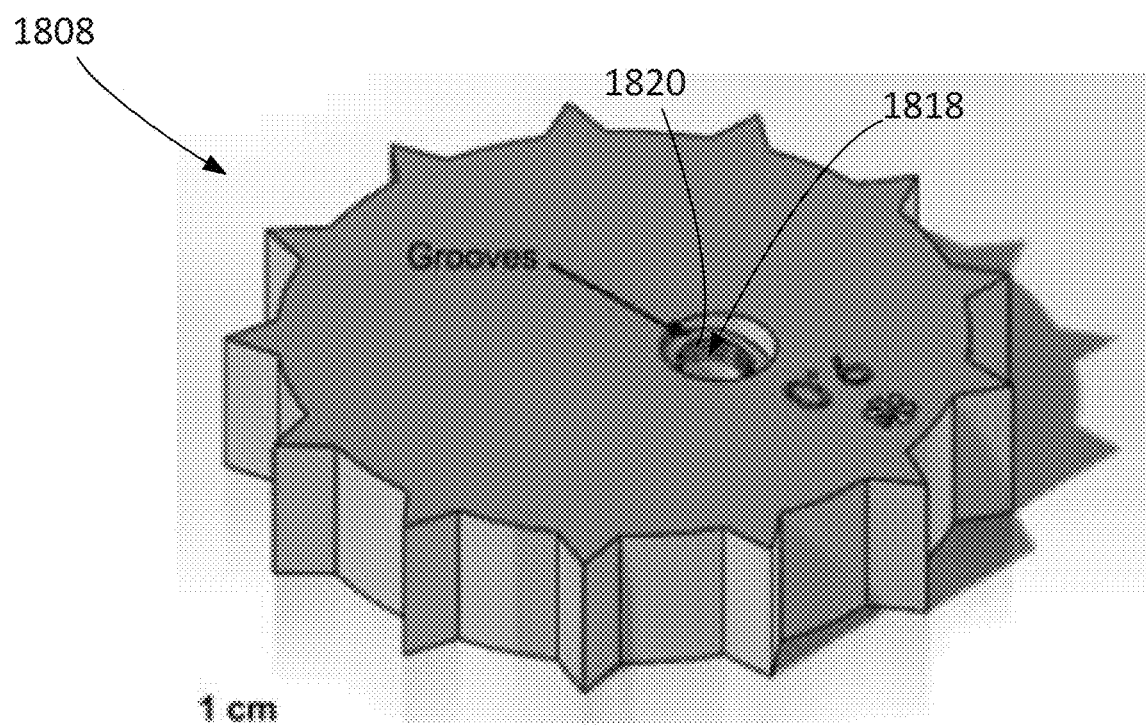
FIG. 18 is a perspective view of a guide block of a guide system in accordance with the present disclosure.

For example, referring now to FIGS. 17 and 18, a detachable trajectory stem 1710 and a corresponding guide block 1808 are illustrated. The trajectory stem 1710 is similar to the trajectory stem 1610, but is selectively detachable from the guide block 1808. The trajectory stem 1710 includes a connection portion 1712, a pair of displaceable prongs 1714, a set of movable teeth 1716, and a guide hole 1760. The connection portion 1712 is configured to selectively engage the guide block 1808, as will be described below.

The guide block 1808 is similar to the guide block 208, but includes a trajectory stem aperture 1818 in place of a guide hole. The trajectory stem aperture 1818 is sized to receive the connection portion 1712 of the trajectory stem 1710. The trajectory stem aperture 1818 further includes engagement grooves 1820, configured to engage the movable teeth 1716 of the trajectory stem 1710. Accordingly, the trajectory stem aperture is configured to receive the given detachable trajectory stem 1710 and orient the guide hole 1760 along an angle of trajectory with respect to a central axis of the guide block 1808.

During use, the trajectory stem 1710 may be attached to the guide block 1808 by inserting the connection portion 1712 into the trajectory stem aperture 1818 of the guide block 1808. As the connection portion 1712 is inserted, the movable teeth 1716 engage the engagement grooves 1820 of the trajectory stem aperture 1818, thereby retaining the trajectory stem 1710 within the trajectory stem aperture 1818. Then, if the surgeon decides to remove the trajectory stem 1710 from the trajectory stem aperture 1818, the surgeon may press the prongs 1714 toward each other, thereby disengaging the movable teeth 1716 from the engagement grooves 1820.

Figure 19:
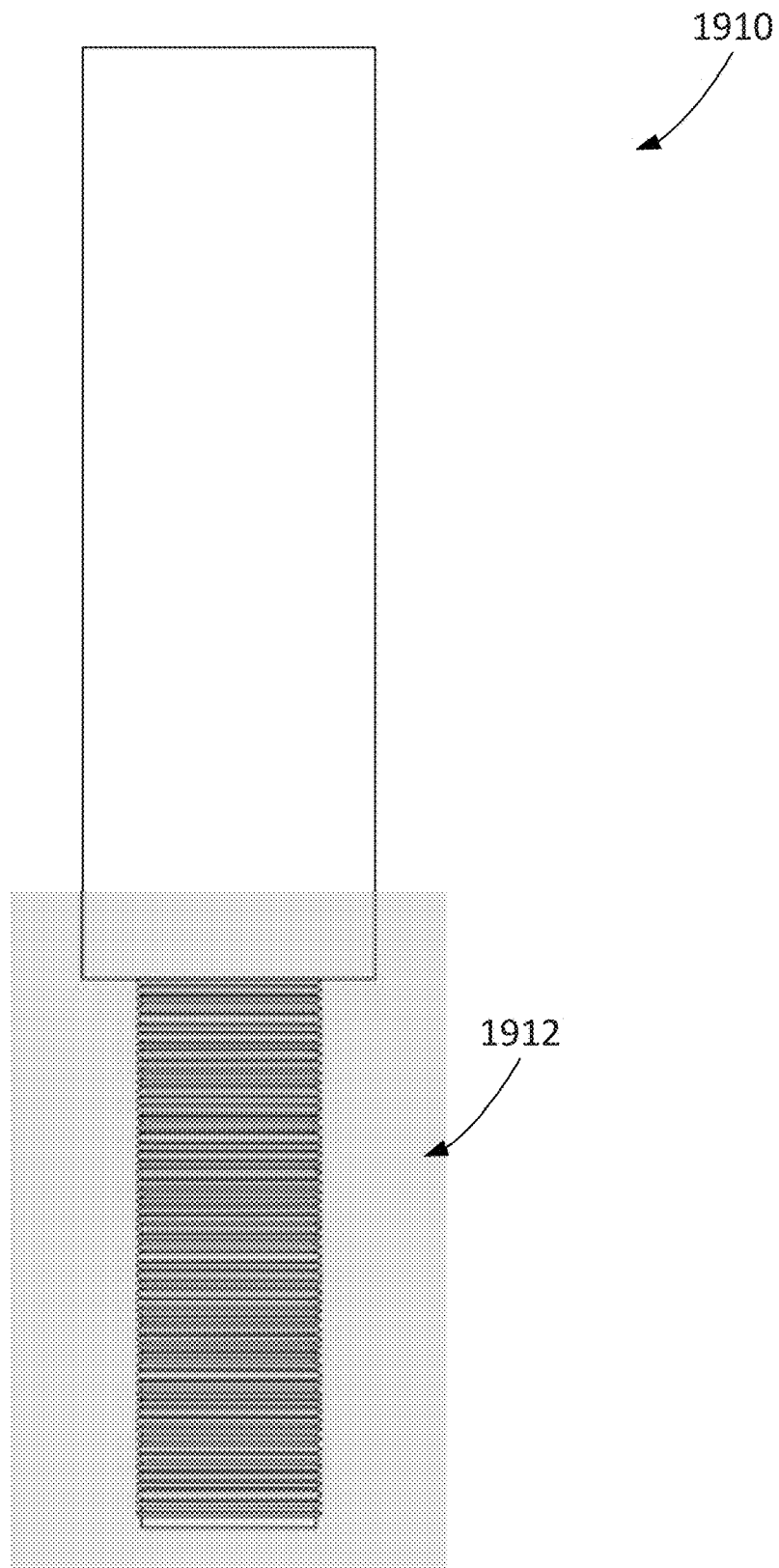
FIG. 19 is a front elevational view of a detachable trajectory stem of a guide system in accordance with the present disclosure.

Referring now to FIG. 19, another detachable trajectory stem 1910 is illustrated. The trajectory stem 1910 is similar to the trajectory stem 1710, but alternatively includes a toothed or threaded portion 1912. The toothed or threaded portion 1912 may be configured to engage corresponding teeth or threads of a trajectory stem aperture, similar to the trajectory stem aperture 1818, to selectively couple the trajectory stem 1910 to the guide block when inserted therein.

The teeth or threads of the toothed or threaded portion may be configured to screw into the trajectory stem aperture or, in some cases, may be configured to, in combination with corresponding teeth of the trajectory stem aperture, function similar to a zip-tie. Accordingly, the trajectory stem 1910 would be locked into place once inserted. In some instances, similar to a zip-tie, there may be a removal feature added to increase versatility of inner diameter through stem changing without replacement of the guide block.

Additionally, to aid in providing a consistent depth of insertion of the trajectory stem 1910, thereby allowing for more precise depth tracking of instruments used during procedures, the top face of each corresponding guide block may be modified to include an inset. The inset may be the size of a connection portion 1912 of the trajectory stem 1910, and arranged at the same angle of the hole. When inserted, the trajectory stem 1910 may fit flush into this inset, thereby providing an accurate marker for instrument depth.

Figure 20:
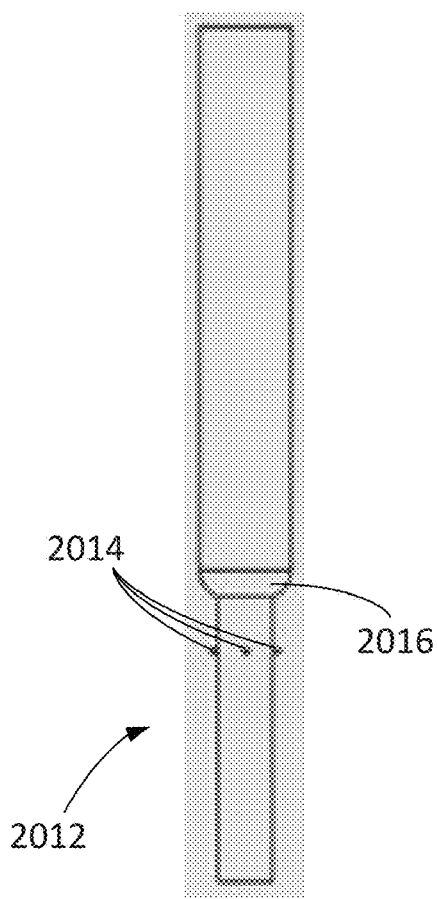
FIG. 20 is a front elevational view of a detachable trajectory stem of a guide system in accordance with the present disclosure.
Figure 21:
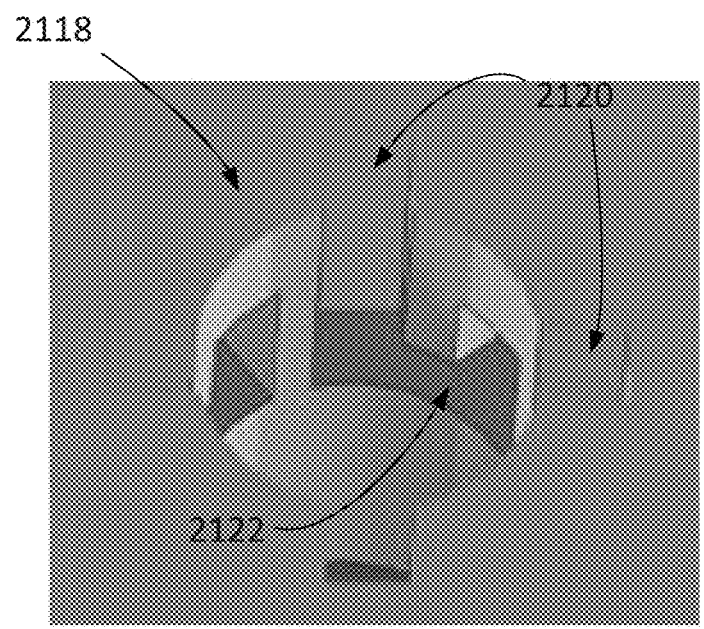
FIG. 21 is a perspective view of a trajectory stem aperture of a guide system in accordance with the present disclosure.

Referring now to FIGS. 20 and 21, another detachable trajectory stem 2010 and a corresponding trajectory stem aperture 2118 are illustrated. The trajectory stem 2010 is similar to the trajectory stems 1710 and 1910 discussed above, with the connection portion 2012 alternatively including a plurality of pegs 2014 protruding therefrom. The plurality of pegs 2014 are circumferentially-spaced around the connection portion 2012, and are configured to engage the trajectory stem aperture 2118.

The trajectory stem aperture 2118 is configured to receive and selectively engage the connection portion 2012 of the trajectory stem 2010. The trajectory stem aperture 2118 includes a plurality of slots 2120, each configured to receive a corresponding one of the pegs 2014 of the trajectory stem 2010 to selectively couple the trajectory stem 2010 to the trajectory stem aperture 2118. The slots 2120 each further include a locking portion 2122, configured to lock the trajectory stem 2010 within the trajectory stem aperture 2118.

Accordingly, during use, the surgeon may insert the connection portion 2012 into the trajectory stem aperture 2118, with the pegs 2014 being inserted into the corresponding slots 2120. Then, once the connection portion 2012 is inserted, the trajectory stem 2010 may be twisted, thereby sliding the pegs 2014 into the locking portions 2122 of the slots 2120, and locking the trajectory stem 2010 within the trajectory stem aperture 2118. Due to the rigidity of the slots 2120, this trajectory stem/aperture combination provides a consistent instrument depth marker.

In some instances, a rubber ring 2016 may be added to the trajectory stem 2010 to provide a constant counterforce to the guide to keep the pegs 2014 locked within the upwardly disposed section of the locking portion 2122. Alternatively, the slots 2120 may include angled walls (not shown). The angled walls may allow for the pegs 2014 to be snap-fit within the slots 2120.

Figure 22A:
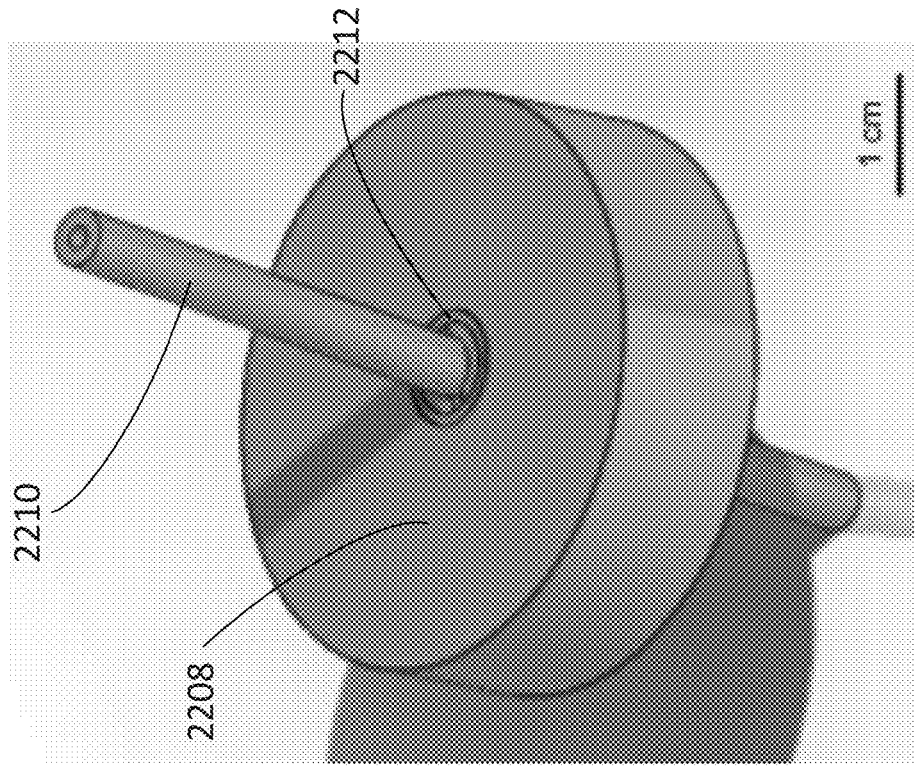
FIG. 22A is a perspective view of a guide block and detachable trajectory stem of a guide system in accordance with the present disclosure.
Figure 22B:
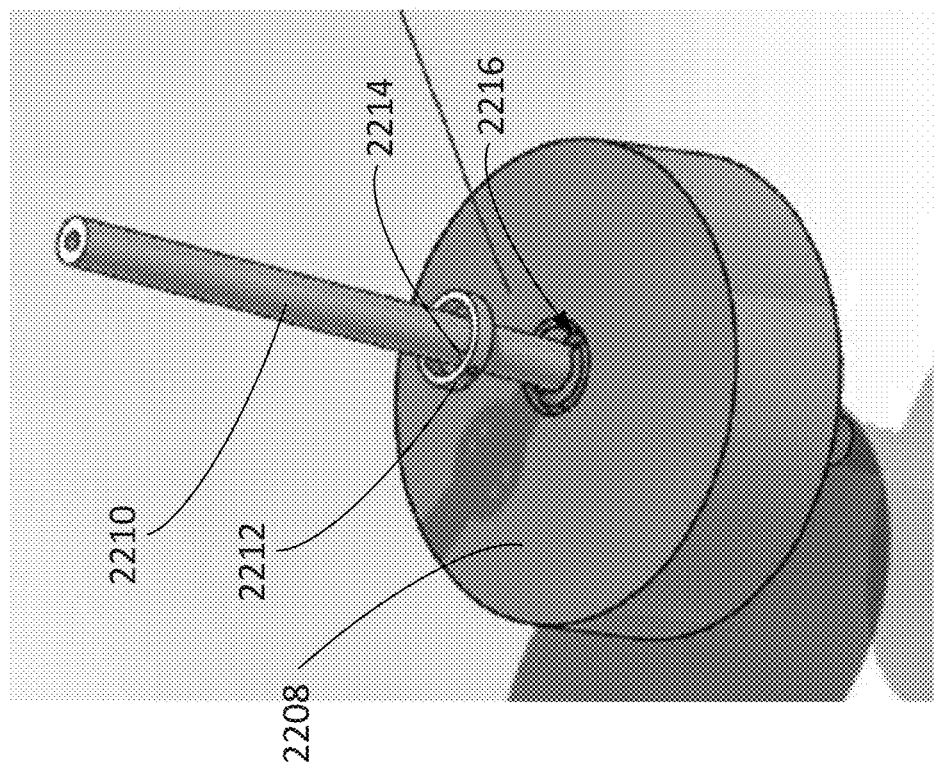
FIG. 22B is a perspective view of the guide block and detachable trajectory stem of FIG. 22A.

Referring now to FIGS. 22A and 22B, another detachable trajectory stem 2210 and corresponding guide block 2208 are illustrated. The trajectory stem 2210 includes a locking ring 2212 that is attached to the trajectory stem 2210 via a pair of pegs 2214. The pair of pegs 2214 are arranged on opposite sides of the trajectory stem 2210. The guide block 2208 further includes a corresponding ring slot 2216, enveloping the trajectory stem aperture (hidden by trajectory stem 2210 in FIGS. 22A and 22B) and configured to receive the locking ring 2212.

Accordingly, during use, the surgeon inserts the locking ring 2212 of the trajectory stem 2210 into place within the ring slot 2216, thereby locking the trajectory stem 2210 within the trajectory stem aperture of the guide block 2208 and providing a consistent length of the trajectory stem 2210 to remain above the guide block 2208.

Due to the pair of pegs 2214 being arranged on opposite sides of the trajectory stem 2210, the locking ring 2212 can be aligned perpendicularly to the surface of the guide block 2208, regardless of the angle of the trajectory stem aperture.

Accordingly, during use of any of the detachable trajectory stems 1710, 1910, 2010, 2210 discussed above, the surgeon may select an appropriate detachable trajectory stem from a plurality of detachable trajectory stems, each having a guide hole of differing diameter to provide a selectable, predetermined clearance diameter to allow for drills and medical instruments of varying size to be used.

It should be appreciated that the guide systems 200, 1100 can be sized and manufactured accordingly for their intended use. For example, in some instances, the guide systems 200, 1100 may be sized to fit under a head coil during an MRI analysis. In some instances, the guide systems 200, 1100 may be disposable medical devices for use in neurosurgeries in a magnetic resonance (MR) setting.

Further, in some instances, the methods of use described herein for the guide system 200, 1100 may be at least partially automated using a hydraulic, pneumatic, or electronic adjustment system to adjust the adjustment rings 206, 1106 and guide blocks 208, 1108 with respect to the base components 202, 1102. For example, the plurality of ring adjustment controls of the guide systems 200, 100 (i.e., the locating protrusions 252 and locating notches 244 of the guide system 200 and the alignment holes 1128 and the alignment tab 1130 of the guide system 1100) may additionally or alternatively include a hydraulic system configured to selectively fix the adjustment ring 206, 1106 with respect to the base 202, 1102. Similarly, for example, the plurality of block adjustment controls of the guide systems 200, 1100 (i.e., the locating protrusions 262 and locating notches 255 of the guide system 200 and the alignment holes 1132 and the alignment tab 1140 of the guide system 1100) may additionally or alternatively include a hydraulic system configured to selectively fix the guide block 208, 1108 with respect to the adjustment ring 206, 1106.

It should also be appreciated that the guide systems 200, 1100 may comprise robust materials configured to support forces incurred during surgery and undergo sterilization procedures, such as, for example, autoclave or gamma radiation. The guide systems 200, 1100 may further comprise materials that are MRI compatible and radiopaque. Further, the guide systems may be constructed with tolerances that prevent the various components from shifting or becoming loose during surgery.

Figure 23:
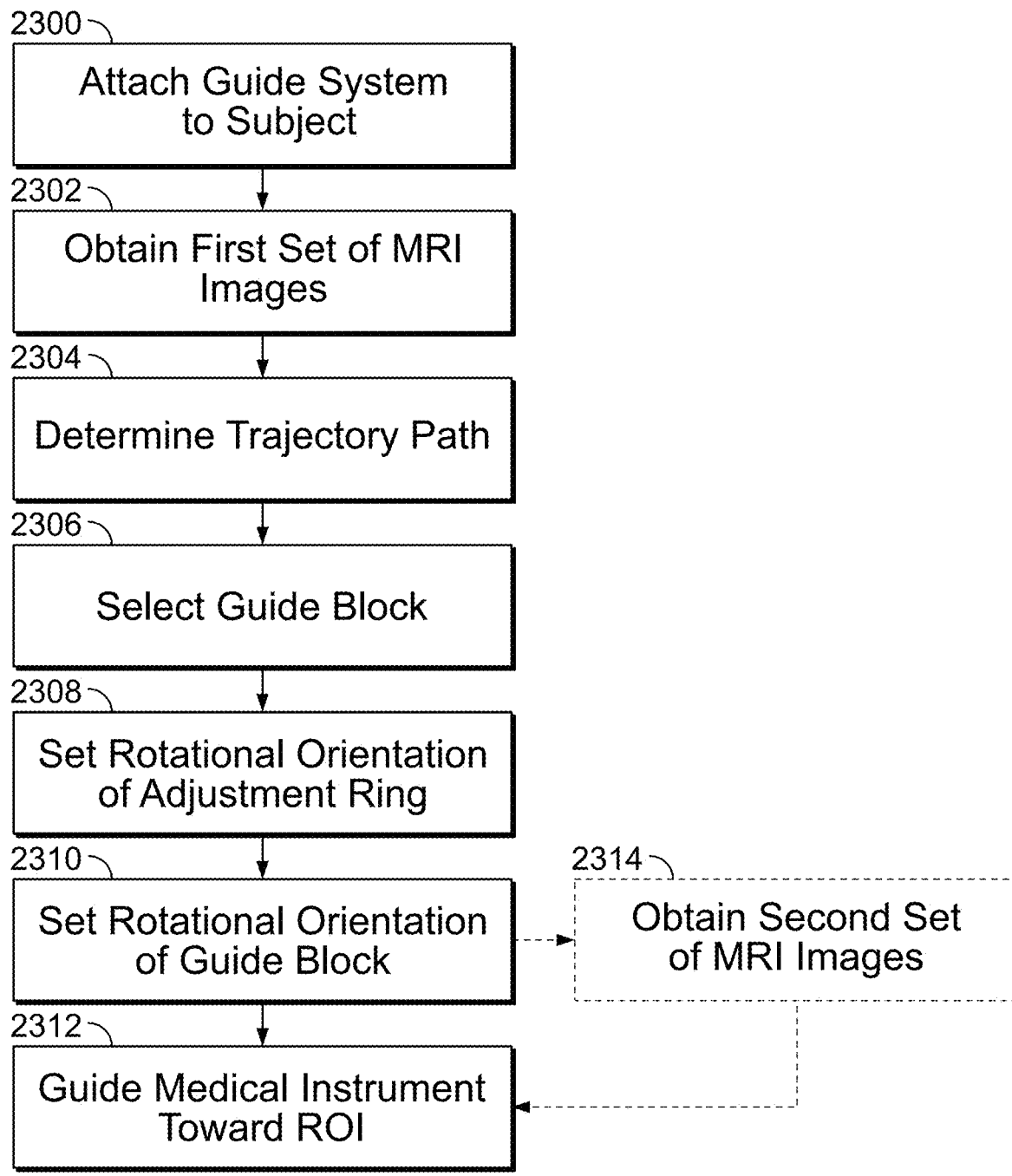
FIG. 23 is a flow chart setting forth some non-limiting, examples of steps for using the systems described herein.

Referring to FIG. 23, a flow chart is provided to set forth some, non-limiting steps of a method for using the systems described above. At process block 2300, either of the guide systems 200, 1100 can be attached to the subject. This attachment can be achieved using bone screws 221, 1126 to attach the base 202, 1102 to the skull or any other anatomical area of the subject, as described above. At process block 2302, a first set of MRI images may be obtained using the MRI system 100 described above or any other suitable real-time MRI system. The first set of MRI images can be used to orient and locate the guide system 200, 1100 in space with respect to a region of interest within a brain or other anatomical area of the subject. At process block 2304, the surgeon may then determine a trajectory path based on the first set of MRI images.

At process block 2306, the surgeon may then select a guide block 208, 1108 of the plurality of guide blocks 208, 1108 based on the determined trajectory path. The selection of the guide block 208, 1108 may comprise the surgeon selecting the guide block 208, 1108 having a corresponding angle of trajectory for the determined trajectory path.

At process block 2308, the surgeon may set a rotational orientation of the adjustment ring 206, 1106 with respect to the base 202, 1102 based on the determined trajectory path. The setting of the rotational orientation of the adjustment ring 206, 1106 may comprise aligning an alignment marker of one of the adjustment ring 206, 1106 and the base 202, 1102 with a predetermined one of a plurality of alignment indicators on the other of the adjustment ring 206, 1106 and the base 202, 1102.

At process block 2310, the surgeon may set a rotational orientation of the selected guide block 208, 1108 with respect to the adjustment ring 206, 1106 based on the determined trajectory path. The setting of the rotational orientation of the selected guide block 208, 1108 may comprise aligning an alignment marker of one of the guide block 208, 1108 and the adjustment ring 206, 1106 with a predetermined one of a plurality of alignment indicators arranged on the other of the guide block 208, 1108 and the adjustment ring 206, 1106.

At process block 2312, the surgeon may then guide an elongated medical instrument through the guide hole 260, 1142 of the selected guide block 208, 1108 toward the region of interest to perform a desired surgery, operation, treatment or other medical procedure.

In some instances, at process block 2314, prior to guiding the elongated medical instrument through the guide hole 260, 1142 of the selected guide block 208, 1108, a second set of MRI images may be obtained using the MRI system 100 or any other suitable real-time MRI system. The surgeon may then use the second set of MRI images to confirm the determined trajectory path of the elongated medical instrument.

Thus, the present disclosure provides systems and methods which allow for a surgeon to quickly set a trajectory path of a catheter or other elongated object during an operation, while only performing two MRI scans of the subject to ensure accuracy of the guide system. As such, the systems and methods provided herein allow for increased user friendliness in the operating room and lowered labor costs for surgical teams by reducing both setup time and the number of MRI scans performed during operation.

The present invention has been described in terms of one or more preferred embodiments, and it should be appreciated that many equivalents, alternatives, variations, and modifications, aside from those expressly stated, are possible and within the scope of the invention.

What is claimed is:

1. A guide system for guiding an interventional medical instrument toward a region of interest (ROI) along a predetermined trajectory path, the guide system comprising:
   a base configured to be attached to a subject proximate to the ROI;
   an adjustment ring configured to be selectively fixed in one of a plurality of incremental rotational orientations with respect to the base; and
   a plurality of guide blocks, wherein each guide block of the plurality of guide blocks is configured to be selectively fixed in one of a plurality of incremental rotational orientations with respect to the adjustment ring, and wherein each guide block includes a central axis and a guide hole configured to guide the interventional medical instrument therethrough along an angle of trajectory with respect to the central axis of the corresponding guide block;
   wherein each of the plurality of guide blocks includes at least one of differing angles of trajectory or differing locations of the guide hole from others of the plurality of guide blocks to provide a selectable, predetermined location of the guide hole and angle of trajectory when a given guide block of the plurality of guide blocks is received in the base.

2. The guide system of claim 1, further comprising:
   a plurality of ring adjustment controls configured to selectively fix the adjustment ring in a desired rotational orientation with respect to the base; and
   a plurality of block adjustment controls configured to selectively fix the guide block in the desired rotational orientation with respect to the adjustment ring.

3. The guide system of claim 2, wherein the plurality of ring adjustment controls comprises a plurality of locating notches and a corresponding plurality of locating protrusions, wherein the plurality of locating notches are arranged on a ring holder that is coupled to the base and wherein the plurality of locating protrusions are arranged on the adjustment ring and are configured to engage the plurality of locating notches.

4. The guide system of claim 2, wherein the plurality of ring adjustment controls comprises a plurality of alignment holes arranged on the base and a corresponding alignment tab arranged on the adjustment ring and configured to engage a predetermined one of the plurality of alignment holes.

5. The guide system of claim 2, wherein the plurality of block adjustment controls comprises a plurality of locating notches and a corresponding plurality of locating protrusions, wherein the locating notches are arranged on the adjustment ring, and the plurality of locating protrusions are arranged on each of the plurality of guide blocks and are configured to engage the plurality of locating notches.

6. The guide system of claim 2, wherein the plurality of block adjustment controls comprises a plurality of alignment holes arranged on the adjustment ring and a corresponding alignment tab arranged on the guide block and configured to engage a predetermined one of the plurality of alignment holes.

7. The guide system of claim 2, wherein the plurality of ring adjustment controls provides a first prime number of unique adjustment ring rotational orientations with respect to the base, and wherein the plurality of block adjustment controls provides a second prime number of unique guide block rotational orientations with respect to the adjustment ring, and wherein the first prime number is different than the second prime number.

8. The guide system of claim 7, wherein the plurality of ring adjustment controls provides seventeen unique adjustment ring rotational orientations with respect to the base and the plurality of block adjustment controls provides thirteen unique guide block rotational orientations with respect to the adjustment ring.

9. The guide system of claim 2, further comprising a plurality of indicators configured to indicate an orientation of the adjustment ring with respect to the base for each of the plurality of ring adjustment controls.

10. The guide system of claim 9, wherein the plurality of indicators are arranged on one of the base and the adjustment ring and the other of the base and the adjustment ring includes an alignment marker configured to be aligned with a predetermined one of the plurality of indicators to arrange the adjustment ring in the desired rotational orientation with respect to the base.

11. The guide system of claim 2, further comprising a plurality of indicators configured to indicate an orientation of the guide block with respect to the adjustment ring for each of the plurality of block adjustment controls.

12. The guide system of claim 11, wherein the plurality of indicators are arrange on one of the guide block and the adjustment ring and the other of the guide block and the adjustment ring includes an alignment marker configured to be aligned with a predetermined one of the plurality of indicators to arrange the guide block in the desired rotational orientation with respect to the adjustment ring.

13. The guide system of claim 1, wherein the base includes a plurality of stilts configured to couple the base to the subject.

14. The guide system of claim 1, wherein the base includes a flange having a curved lower surface configured to conform to a surface of a skull of the subject.

15. The guide system of claim 1, wherein each of the plurality of guide blocks includes a corresponding integral trajectory stem configured to effectively elongate the corresponding guide hole.

16. A guide system for guiding an elongated medical instrument toward a region of interest along a predetermined trajectory path, the guide system comprising:
   a base configured to be attached to a subject to receive the elongated medical instrument during an interventional medical procedure;
   an adjustment ring engaging the base;
   a plurality of ring adjustment controls configured to selectively fix the adjustment ring in a desired rotational orientation with respect to the base;
   a plurality of guide blocks, wherein each guide block of the plurality of guide blocks includes a central axis and a guide hole configured to guide the elongated medical instrument therethrough along an angle of trajectory with respect to the central axis of the corresponding guide block and into the subject to perform the interventional medical procedure, wherein the guide holes of the plurality of guide blocks provide at least one of a different angle of trajectory or a different location within a given guide block;

a plurality of block adjustment controls configured to selectively fix the given guide block in a desired rotational orientation with respect to the adjustment ring to present at least one of a unique angle of trajectory or location of the guide hole through which to receive the elongated medical instrument during the interventional medical procedure.

17. The guide system of claim 16, wherein the plurality of ring adjustment controls provides a first prime number of unique adjustment ring rotational orientations with respect to the base and the plurality of block adjustment controls provides a second prime number of unique guide block rotational orientations with respect to the adjustment ring, and wherein the first prime number is different than the second prime number.

18. The guide system of claim 16, further comprising a plurality of indicators disposed on at least one of the base and the adjustment ring and configured to indicate an orientation of the adjustment ring with respect to the base.

19. The guide system of claim 16, further comprising a plurality of indicators disposed on at least one of the adjustment ring or the guide block and configured to indicate an orientation of the guide block with respect to the adjustment ring.

20. The guide system of claim 16, wherein the guide system is composed of material or materials that is safe for use within a magnetic resonance imaging (MRI) system.

21. A guide system for guiding an interventional medical instrument toward a region of interest (ROI) along a predetermined trajectory path, the guide system comprising:

a base configured to be attached to a subject proximate to the ROI;

an adjustment ring configured to be selectively fixed in one of a plurality of incremental rotational orientations with respect to the base;

a plurality of detachable trajectory stems, each having a guide hole; and a plurality of guide blocks, each guide block configured to be selectively fixed in one of a plurality of incremental rotational orientations with respect to the adjustment ring and including a central axis and a trajectory stem aperture, the trajectory stem aperture being configured to receive a given detachable trajectory stem of the plurality of detachable trajectory stems and orient the corresponding guide hole of the given detachable trajectory stem along an angle of trajectory with respect to the central axis of the corresponding guide block;

wherein each of the plurality of guide blocks includes at least one of differing angles of trajectory or differing locations of the guide hole from others of the plurality of guide blocks to provide a selectable, predetermined location of the guide hole and angle of trajectory when a given guide block of the plurality of guide blocks is received in the base, wherein the plurality of detachable trajectory stems each include a connection portion configured to selectively couple the given detachable trajectory stem to the given guide block.

22. The guide system of claim 21, wherein the guide holes of each of the plurality of detachable trajectory stems have a guide hole diameter, and each of the plurality of detachable trajectory stems includes a differing guide hole diameter from others of the plurality of detachable trajectory stems to provide a selectable, predetermined clearance diameter for the interventional medical instrument when the given detachable trajectory stem is received in the trajectory stem aperture of the given guide block.

23. The guide system of claim 21, wherein the connection portion of the given detachable trajectory stem and the trajectory stem aperture of the given guide block each include teeth configured to engage each other to selectively couple the given detachable trajectory stem to the given guide block.

24. The guide system of claim 21, wherein the connection portion of the given detachable trajectory stem includes a plurality of pegs and the trajectory stem aperture of the given guide block includes a corresponding plurality of slots configured to receive the plurality of pegs to selectively couple the given detachable trajectory stem to the given guide block.

25. The guide system of claim 21, wherein the connection portion of the given detachable trajectory stem includes a locking ring and the trajectory stem aperture of the given guide block includes a corresponding ring slot configured to receive the locking ring to selectively couple the given detachable trajectory stem to the given guide block.

26. The guide system of claim 21, wherein the trajectory stem aperture of the given guide block includes a set of grooves and the connection portion of the given detachable trajectory stem includes a set of movable teeth configured to selectively engage the set of grooves of the given guide block to selectively couple the given trajectory stem to the given guide block.

* * * * *

UNITED STATES PATENT AND TRADEMARK OFFICE
CERTIFICATE OF CORRECTION

PATENT NO. : 11,179,056 B2
APPLICATION NO. : 16/100605
DATED : November 23, 2021
INVENTOR(S) : Caitlin R. Randell et al.

Page 1 of 1

It is certified that error appears in the above-identified patent and that said Letters Patent is hereby corrected as shown below:

In the Specification

Column 5, Line 16, "the/and Q" should be --the I and Q--.

Signed and Sealed this
First Day of March, 2022

Drew Hirshfeld
*Performing the Functions and Duties of the
Under Secretary of Commerce for Intellectual Property and
Director of the United States Patent and Trademark Office*